(12) United States Patent
Yum et al.

(10) Patent No.: US 8,246,977 B2
(45) Date of Patent: *Aug. 21, 2012

(54) TRANSDERMAL DELIVERY SYSTEMS

(75) Inventors: Su Il Yum, Los Altos, CA (US); Felix Theeuwes, Los Altos Hills, CA (US)

(73) Assignee: Durect Corporation, Cupertino, CA (US)

( * ) Notice: Subject to any disclaimer, the term of this patent is extended or adjusted under 35 U.S.C. 154(b) by 505 days.

This patent is subject to a terminal disclaimer.

(21) Appl. No.: 11/665,813

(22) PCT Filed: Oct. 21, 2005

(86) PCT No.: PCT/US2005/038086
§ 371 (c)(1),
(2), (4) Date: Apr. 19, 2007

(87) PCT Pub. No.: WO2006/047362
PCT Pub. Date: May 4, 2006

(65) Prior Publication Data
US 2008/0206314 A1 Aug. 28, 2008

Related U.S. Application Data

(60) Provisional application No. 60/621,123, filed on Oct. 21, 2004.

(51) Int. Cl.
*A61K 9/70* (2006.01)
*A61K 31/445* (2006.01)

(52) U.S. Cl. ........ 424/448; 424/449; 424/443; 514/317; 514/326; 514/329

(58) Field of Classification Search .................. None
See application file for complete search history.

(56) References Cited

U.S. PATENT DOCUMENTS

| | | |
|---|---|---|
| 4,031,894 A | 6/1977 | Urquhart et al. |
| 4,060,084 A | 11/1977 | Chandrasekaran et al. |
| 4,201,211 A | 5/1980 | Chandrasekaran et al. |
| 4,409,206 A | 10/1983 | Stricker |
| 4,435,180 A | 3/1984 | Leeper |
| 4,559,222 A | 12/1985 | Enscore et al. |
| 4,568,343 A | 2/1986 | Leeper et al. |
| 4,573,995 A | 3/1986 | Chen et al. |
| 4,573,996 A | 3/1986 | Kwiatek et al. |
| 4,588,580 A * | 5/1986 | Gale et al. ............. 424/449 |
| 4,601,893 A | 7/1986 | Cardinal |
| 4,626,539 A | 12/1986 | Aungst et al. |
| 4,638,043 A | 1/1987 | Szycher et al. |
| 4,645,502 A | 2/1987 | Gale et al. |
| 4,666,441 A | 5/1987 | Andriola et al. |
| 4,710,191 A | 12/1987 | Kwiatek et al. |
| 4,725,272 A * | 2/1988 | Gale ....................... 424/448 |
| 4,725,439 A | 2/1988 | Campbell et al. |
| 4,746,515 A | 5/1988 | Cheng et al. |
| 4,747,845 A | 5/1988 | Korol |
| 4,756,710 A | 7/1988 | Bondi et al. |
| 4,781,924 A | 11/1988 | Lee et al. |
| 4,788,062 A | 11/1988 | Gale et al. |
| 4,806,341 A | 2/1989 | Chien et al. |
| 4,808,414 A | 2/1989 | Peck et al. |
| 4,816,258 A | 3/1989 | Nedberge et al. |
| 4,822,802 A | 4/1989 | Levy et al. |
| 4,824,676 A | 4/1989 | Bodor |
| 4,830,860 A | 5/1989 | Ranade |
| 4,834,978 A | 5/1989 | Nuwayser |
| 4,837,026 A | 6/1989 | Rajakhyaksha |
| 4,837,027 A | 6/1989 | Lee et al. |
| 4,863,738 A | 9/1989 | Taskovich |
| 4,877,618 A | 10/1989 | Reed, Jr. |
| 4,879,297 A | 11/1989 | Mahjour et al. |
| 4,900,555 A | 2/1990 | Cheng et al. |
| 4,904,475 A | 2/1990 | Gale et al. |
| 4,906,463 A | 3/1990 | Cleary et al. |
| 4,931,283 A | 6/1990 | Tsuk |
| 4,938,759 A | 7/1990 | Enscore et al. |
| 4,990,339 A | 2/1991 | Scholl et al. |
| 5,006,342 A | 4/1991 | Cleary et al. |
| 5,053,227 A | 10/1991 | Chiang et al. |
| 5,079,008 A | 1/1992 | Sinnreich et al. |

(Continued)

FOREIGN PATENT DOCUMENTS

EP 0427741 1/1998

(Continued)

OTHER PUBLICATIONS

Anesth. Analg 2003; 96: 1234.*
Lipp, R., "Selection and Use of Crystallization Inhibitors for Matrix-type Transdermal Drug-delivery Systems Conatining Sex Steroids" *J. Pharm. Pharmacol.* 50:1343-1349 (1998).
Shaw et al. (1985) "Transdermal Dosage Forms," in Rate Control in Drug Therapy, (Prescott et al. eds), pp: 65-70, Churchill Livingstone, Edinburgh.
Shaw et al. (1991) in Physiology, Biochemistry, and Molecular Biology of the Skin, Second Ed., pp. 1447-1479, Goldsmith, L. A. Ed., Oxford University Press, Oxford, UK.

(Continued)

*Primary Examiner* — David J Blanchard
*Assistant Examiner* — Kyle Purdy

(57) ABSTRACT

Transdermal delivery systems for administering sufentanil through the skin are provided. The systems contain a sufficient amount of sufentanil to induce and maintain a constant state of analgesia when applied to a subject. The systems are characterized as having one or more features including a high degree of dosage form rate control over flux of sufentanil from the system, a high net flux of sufentanil from the system through the skin, lack of a permeation enhancer, an adhesive member demonstrating superior shear time, a low coefficient of variation in the net flux of sufentanil from the system, a high delivery efficiency, and a substantially constant steady state net flux of sufentanil from the system. Methods of using the transdermal delivery systems to administer a sufficient amount of sufentanil to induce and maintain analgesia for extended periods when applied to a subject are also provided.

22 Claims, 11 Drawing Sheets

U.S. PATENT DOCUMENTS

| | | | |
|---|---|---|---|
| 5,132,115 A | 7/1992 | Wolter et al. |
| 5,141,750 A | 8/1992 | Lee et al. |
| 5,149,719 A | 9/1992 | Ferber et al. |
| 5,186,939 A | 2/1993 | Cleary et al. |
| 5,223,261 A | 6/1993 | Nelson et al. |
| 5,229,130 A | 7/1993 | Sharma et al. |
| 5,232,702 A | 8/1993 | Pfister et al. |
| 5,236,714 A | 8/1993 | Lee et al. |
| 5,240,932 A | 8/1993 | Morimoto et al. |
| 5,250,023 A | 10/1993 | Lee et al. |
| 5,252,334 A | 10/1993 | Chiang et al. |
| 5,254,346 A | 10/1993 | Tucker et al. |
| 5,264,219 A | 11/1993 | Godbey et al. |
| 5,300,299 A | 4/1994 | Sweet et al. |
| 5,310,559 A | 5/1994 | Shah et al. |
| 5,342,623 A | 8/1994 | Enscore et al. |
| 5,344,656 A | 9/1994 | Enscore et al. |
| 5,352,457 A | 10/1994 | Jenkins |
| 5,362,497 A | 11/1994 | Yamada et al. |
| 5,372,819 A | 12/1994 | Godbey et al. |
| 5,411,740 A | 5/1995 | Lee et al. |
| 5,446,070 A | 8/1995 | Mantelle |
| 5,458,885 A | 10/1995 | Muller et al. |
| 5,462,745 A | 10/1995 | Enscore et al. |
| 5,474,783 A | 12/1995 | Miranda et al. |
| 5,505,956 A | 4/1996 | Kim et al. |
| 5,613,958 A | 3/1997 | Kochinke et al. |
| 5,614,212 A | 3/1997 | D'Angelo et al. |
| 5,626,866 A | 5/1997 | Ebert et al. |
| 5,629,019 A | 5/1997 | Lee et al. |
| 5,635,203 A | 6/1997 | Gale et al. |
| 5,641,504 A | 6/1997 | Lee et al. |
| 5,656,286 A | 8/1997 | Miranda et al. |
| 5,741,510 A | 4/1998 | Rolf et al. |
| 5,750,137 A | 5/1998 | Taskovich et al. |
| 5,756,117 A | 5/1998 | D'Angelo et al. |
| 5,762,952 A | 6/1998 | Barnhart et al. |
| 5,770,219 A | 6/1998 | Chiang et al. |
| 5,785,991 A | 7/1998 | Burkoth et al. |
| 5,834,010 A | 11/1998 | Quan et al. |
| 5,843,468 A | 12/1998 | Burkoth et al. |
| 5,876,746 A | 3/1999 | Jona et al. |
| 5,879,701 A | 3/1999 | Audett et al. |
| 5,902,603 A | 5/1999 | Chen et al. |
| 5,906,830 A * | 5/1999 | Farinas et al. ................ 424/448 |
| 5,919,473 A | 7/1999 | Elkhoury |
| 5,925,372 A | 7/1999 | Berner et al. |
| 5,948,433 A | 9/1999 | Burton et al. |
| 5,958,446 A | 9/1999 | Miranda et al. |
| 5,972,377 A | 10/1999 | Jona et al. |
| 5,993,849 A | 11/1999 | Assmus et al. |
| 6,004,578 A | 12/1999 | Lee et al. |
| 6,024,976 A | 2/2000 | Miranda et al. |
| 6,063,399 A | 5/2000 | Assmus et al. |
| 6,093,419 A | 7/2000 | Rolf |
| 6,113,921 A | 9/2000 | Friedman et al. |
| 6,139,866 A | 10/2000 | Chono et al. |
| 6,171,294 B1 | 1/2001 | Southam et al. |
| 6,193,996 B1 | 2/2001 | Effing et al. |
| 6,203,817 B1 | 3/2001 | Cormier et al. |
| 6,211,425 B1 | 4/2001 | Takayasu et al. |
| 6,231,885 B1 | 5/2001 | Carrara |
| 6,238,693 B1 | 5/2001 | Luther et al. |
| 6,267,984 B1 | 7/2001 | Beste et al. |
| 6,277,413 B1 | 8/2001 | Sankaram |
| 6,280,766 B1 | 8/2001 | Becher et al. |
| 6,344,211 B1 | 2/2002 | Hille |
| 6,348,210 B1 | 2/2002 | Gale |
| 6,365,178 B1 | 4/2002 | Venkateshwaran et al. |
| 6,375,978 B1 | 4/2002 | Kleiner et al. |
| 6,383,511 B1 | 5/2002 | Cassel |
| 6,425,892 B2 | 7/2002 | Southam et al. |
| 6,428,814 B1 | 8/2002 | Bosch et al. |
| 6,440,513 B1 | 8/2002 | Kibele et al. |
| 6,453,195 B1 | 9/2002 | Thompson |
| 6,461,644 B1 | 10/2002 | Jackson et al. |
| 6,465,004 B1 | 10/2002 | Rossi-Montero et al. |
| 6,541,037 B1 | 4/2003 | Lee et al. |
| 6,582,724 B2 | 6/2003 | Hsu et al. |
| 6,624,138 B1 | 9/2003 | Sung et al. |
| 6,638,528 B1 | 10/2003 | Kanios |
| 6,645,521 B2 | 11/2003 | Cassel |
| 6,660,295 B2 | 12/2003 | Watanabe et al. |
| 6,669,953 B1 | 12/2003 | Kamiyama |
| 6,669,954 B2 | 12/2003 | Crison et al. |
| 6,699,497 B1 | 3/2004 | Van Osdol et al. |
| 6,716,449 B2 | 4/2004 | Oshlack et al. |
| 6,720,001 B2 | 4/2004 | Chen et al. |
| 6,723,337 B1 | 4/2004 | Song et al. |
| 6,737,080 B1 | 5/2004 | Schumann |
| 6,750,291 B2 | 6/2004 | Kim et al. |
| 2001/0033858 A1 * | 10/2001 | Zhang ........................ 424/443 |
| 2001/0053383 A1 | 12/2001 | Miranda et al. |
| 2002/0004065 A1 | 1/2002 | Kanios |
| 2002/0010127 A1 * | 1/2002 | Oshlack et al. ................ 514/2 |
| 2002/0018805 A1 | 2/2002 | Gale |
| 2002/0028235 A1 | 3/2002 | Reed et al. |
| 2002/0034535 A1 | 3/2002 | Kleiner et al. |
| 2002/0077437 A1 | 6/2002 | Silverberg et al. |
| 2002/0098228 A1 | 7/2002 | Tarazi et al. |
| 2002/0106402 A1 | 8/2002 | Hartwig |
| 2002/0119186 A1 | 8/2002 | Zhang et al. |
| 2002/0119187 A1 | 8/2002 | Cantor et al. |
| 2003/0026829 A1 * | 2/2003 | Venkatraman et al. ....... 424/449 |
| 2003/0064093 A1 | 4/2003 | Jordan |
| 2003/0091620 A1 | 5/2003 | Fikstad et al. |
| 2003/0152616 A1 | 8/2003 | Hartwig |
| 2003/0166624 A1 | 9/2003 | Gale et al. |
| 2003/0170295 A1 | 9/2003 | Kim et al. |
| 2003/0170296 A1 | 9/2003 | Sintov et al. |
| 2004/0001882 A1 | 1/2004 | Tisa-Bostedt et al. |
| 2004/0013629 A1 | 1/2004 | Andolino Brandt et al. |
| 2004/0013716 A1 | 1/2004 | Gale et al. |
| 2004/0213832 A1 | 10/2004 | Venkatraman et al. |
| 2005/0095279 A1 | 5/2005 | Gale et al. |
| 2005/0118246 A1 | 6/2005 | Wong et al. |
| 2005/0208117 A1 | 9/2005 | Venkatraman et al. |
| 2007/0202156 A1 | 8/2007 | Saeki et al. |
| 2009/0130190 A1 | 5/2009 | Breitenbach et al. |

FOREIGN PATENT DOCUMENTS

| | | |
|---|---|---|
| EP | 01477164 | 11/2004 |
| EP | 1 552 835 A1 | 7/2005 |
| GB | 2 165 148 A | 4/1986 |
| JP | 61-37725 | 2/1986 |
| JP | 2004-524336 A | 9/2002 |
| WO | 02/074286 | 9/2002 |
| WO | WO 02/074286 | 9/2002 |
| WO | 04/35054 | 4/2004 |
| WO | WO 2007121949 | 1/2007 |
| WO | WO 2007095147 | 8/2007 |

OTHER PUBLICATIONS

Satas (1989) "Acrylic Adhesives", Handbook of Pressure-Sensitive Adhesive Technology, 2nd ed., pp. 396-456 (D. Satas, ed.), Van Nostrand Reinhold, NY.

Moulin et al. "Subcutaneous narcotic infusions for cancer pain: treatment outcome and guidelines for use", (1992) Can. Med. Assoc. J. 146:891-7.

Sjogren et al. "Disappearance of morphine-induced hyperalgesia after discontinuing or substituting morphine with other opioid agonists", 1994, Pain 59:313-316.

Paix et al. "Subcutaneous fentanyl and sufentanil infusion substitution for morphine intolerance in cancer pain management", (1995) Pain 63:263-9.

Roy et al. "Preformulation aspects of transdermal drug delivery systems," in Transdermal and Topical Drug Delivery Systems, Eds. Ghosh, Pfister and Yum, Interpharm Press, Buffalo Grove IL,1997, pp. 139-166.

Southwell et al., "Variations in permeability of human skin within and between specimens," Int. J. Pharmaceutics, 18 (1984) 299-309.

Clotz & Nahata (1991) "Clinical Uses of Fentanyl, Sufentanil, and Alfentanil" Clin. Pharmacol. 10(8):581-593.

Davis & Hadgraft (1991) "Effect of Supersaturation on Membrane Transport: 1. Hydrocortisone Acetate" Int. J. Pharm. 76:1-8.

Duragesic® (Fentanyl Transdermal System) CII. Clinical Trials Poster. ALZA Corporation, Janssen Pharmaceutica Products, L.P., 2003.

Durogesic® http://home.intekom.com/pharm/janssen/duroges.html, Janssen Pharmaceutica (Pty) Ltd, May 19, 1999.

Foreman, et al. (2002) "Predicting Drug Solubility in Transdermal Adhesives" National Starch and Chemical Company, R6290.

Myszka, et al. (1997) "The Impact of Drug Crystallization on Flux in Transdermal Drug-in-Adhesive Formulations" American Association of Pharmaceutical Scientists, 3M Pharmaceuticals, St. Paul, MN, Poster # 2292.

Opposition Response Annex dated Aug. 31, 2011 for EP 1814531 by J.A. Kemp & Co.: Annex to Response to Communication under Rule 79(1) EPC: Technical Information Concerning Polymeric Compositions Relevant to the Opposition Proceedings.

Opposition Response dated Aug. 31, 2011 for EP 1814531 by J.A. Kemp & Co.: Response to Communication under Rule 79(1) EPC dated Apr. 21, 2011 and the Opposition filed by Helm AG.

Roy & Flynn (1988) "Solubility and Related Physicochemical Properties of Narcotic Analgesics" Pharm. Res. 5 (9):580-586.

Roy & Flynn (1990) "Transdermal Delivery of Narcotic Analgesics: pH, Anatomical and Subject Influences on Cutaneous Permeability of Fentanyl and Sufentanil" Pharm. Res. 7(8):842-847.

Roy, et al. (1994) "Transdermal Delivery of Narcotic Analgesics: Comparative Metabolism and Permeability of Human Cadaver Skin and Hairless Mouse Skin" J. Pharm. Sci. 83(12):1723-1728.

Roy, et al. (1996) "Controlled Transdermal Delivery of Fentanyl: Characterizations of Pressure-Sensitive Adhesives for Matrix Patch Design" J. Pharm. Sci. 85(5):491-495.

Shaw & Theeuwes "Estimation of Variability in transdermal flux Due to Skin and TTS" Transdermal Dosage Forms, Second International Conference on Drug Absorption, Edinburgh, Scotland, Sep. 21-23, 1983.

Theeuwes, et al. (1976) "Programmed Diffusional Release Rate from Encapsulated Cosolvent System" J. Pharm. Sci. 65(5):648-652.

Yum, et al. (1994) "Permeation Enhancement with Ethanol: Mechanism of Action through Skin" Drug Permeation Enhancement: Theory and Applications, Ed. Hsieh, Marcel Dekker, Inc., Chapter 8, pp. 143-170.

English language translation of Office Action dated Mar. 6, 2012, from Japanese Application No. 2007-538106, which is a family member of the present application.

Decision to Discontinue the Opposition Proceedings, EPO Form 2352 12.07, for European Patent Application No. 05815696.9, dated Feb. 10, 2012.

Official Withdrawal of Opposition of European Patent Application No. 05815696.9, sent to the European Patent Office from Helm AG on Jan. 31, 2012.

Preliminary Opinion of Opposition Division for European Patent Application No. 05815696.9, dated Dec. 1, 2011.

Forth, et al. Allgemeine und Spezielle Pharmakologie und Toxikologie: Für Studenten der Medizin, Pharmazie, Chemie, Biologie sowie für Ärtze und Apotheker. Bibliographisches Institut Mannheim/Wien/Zürich, 1975, pp. 66-68.

Ghosch, et al. "Materials Selection for Transdermal Drug Delivery Systems" Transdermal and Topical Drug Delivery Systems, Interpharm Press, 1997, p. 263.

Notice of Opposition to European Patent No. EP 1814531 B1 "Transdermal Delivery Systems" Issued Jun. 16, 2010.

Pfeifer, et al. "Transdermale Therapeutische Systeme" Biopiarmazie: Pharmakokinetik—Bio verfügbarkeit—Biotransformation, Ullstein/Mosby-Verlag, 1995, pp. 187-191.

* cited by examiner

TRANSDERMAL DELIVERY SYSTEMS

This application is a national stage entry of PCT/US05/38086, filed Oct. 21, 2005, which claims from the benefit of U.S. Provisional Application No. 60/621,123, filed on Oct. 21, 2004.

FIELD OF THE INVENTION

The invention relates generally to transdermal delivery systems, and more particularly to transdermal delivery systems for administering sufentanil through the skin. The transdermal delivery systems can be used to administer sufentanil to an individual over an extended period of time to provide an analgesic effect.

BACKGROUND OF THE INVENTION

Many medications are used for the treatment of pain, ranging from well known, over-the-counter compounds such as aspirin, acetaminophen, ibuprofen and other non-steroidal anti-inflammatory compounds to the newly developed chemical entities such as the cyclooxygenase II inhibitor compounds. Opiates in various forms, including opium, heroine and morphine that derive from the opium poppy, have very powerful analgesic properties. Opiates have been widely used for anesthesia as well for the treatment of pain, especially where the pain is very severe. In addition to these natural opiates, many synthetic opioids have since been synthesized including methadone, fentanyl and congeners of fentanyl such as sufentanil, alfentanil, lofentanil, carfentanil, remifentanil, etc. Of the opioids, morphine is still the drug of choice for management of pain at least in part due to its low cost, the ability of the drug to provide relief from pain of a variety of origins, and the vast experience with this drug. Despite its therapeutic advantages and vast experience with the drug, many pain management experts believe that morphine and other opioids are under-prescribed for patients who require long-term pain therapy.

One reason for under prescription is the risk of the side effects associated with long-term administration of opioids in general, such as development of opiate tolerance, dependence, constipation, and/or other undesirable side effects (see, e.g., Moulin et al. (1992) Can Med. Assoc. J. 146:891-7). Patients who develop opioid tolerance require increased doses to achieve a satisfactory analgesic effect and risk the development of further undesirable side effects such as respiratory depression, which can be life threatening. Physical dependence, which is related to factors such as the dose administered and the length of the administration period, can generally only be resolved by discontinuing opioid administration, which in turn results in the onset of severely painful withdrawal symptoms. Other side effects that can be associated with administration of opioids include reduced cough reflex, bronchial spasms, nausea, vomiting, peripheral vasodilation, orthostatic hypotension, vagal impact on the heart, contraction of smooth muscles (sphincters), reduced peristaltic motility in the gastrointestinal tract (e.g., constipation), urinary retention, changes in regulation of body temperature and sleep pattern, and release of histamine, adrenalin, and anti-diuretic hormone. The negative effects on respiratory function especially impact postoperative patients, who are particularly susceptible to depression of respiratory function. Even where the concerns regarding side effects might be outweighed by the serious need for pain relief as in terminally ill patients, many doctors still avoid prescribing opioids due to concerns of abuse of surplus medication by others in contact with the patient, or even that their frequent prescription of the drug might lead to criminal investigation.

In addition to the disadvantages listed above pertaining to opioids in general, morphine itself has also been associated with particular side effects, at times so severe as to make such therapy intolerable, especially for patients who are on long-term pain therapy or who require high doses of medication to obtain relief. Some of these side effects associated with morphine usage, particularly at high doses, include nausea and vomiting and severe constipation. In addition, Sjorgen et al. (1994 Pain 59:313-316) have reported the phenomena of hyperalgesia (increased response to certain stimulus which is not normally painful), allodynia (sensation of pain felt even when stimulus is not normally painful) and myoclonus associated with morphine use. It has thus been hypothesized that morphine and its metabolites may induce such abnormal sensitivity.

Fentanyl and its congeners were originally developed as anesthesia agents, and are generally used in the United States for the limited purposes of intravenous administration in balanced general anesthesia, as a primary anesthetic, or, in the case of sufentanil, for epidural administration during labor and delivery. However, these drugs also have powerful analgesic properties and are several hundred- to several thousand-times more potent than morphine depending on the particular congener. A few studies have in fact suggested that fentanyl and its congeners be used instead of morphine due to their increased potency and decreased side effects relative to morphine (see e.g., Sjorgen et al. (1994) Pain 59:313-316). Fentanyl and its congeners are, however, more difficult to administer than morphine since they are not orally absorbed, are extremely potent (requiring very precise, accurate dosing of small amounts) and have very short half lives in the body thus requiring frequent dosing. For these reasons, conventional methods for delivery of opioid analgesics are deemed inadequate to meet these delivery requirements.

For example, fentanyl has been administered in single, small intravenous doses, but this method of administration, besides being impractical for long-term therapy, results in a short duration of action and rapid recovery due to a redistribution into fat stores and a rapid decline in plasma concentration. While subcutaneous infusion of fentanyl and sufentanil have been the subject of experimentation on a limited basis, such infusion methods are impractical as long-term pain therapies. For example, subcutaneous fentanyl and sufentanil delivery has been used as an alternative therapy in a small number of patients who suffered significant side effects associated with administration of morphine. Paix et al. (1995) Pain 63:263-9. In these therapies, the drug was infused into the subcutaneous space in relatively low drug concentrations and at relatively large volume rates (e.g., on the order of 3 mL/day to 40 mL/day) via an external syringe driver. These treatment approaches have several major disadvantages that render them impractical for long-term therapy. First, provision of drug from an external source adversely affects mobility of the patient and is therefore inconvenient for ambulatory patients, increases the risk of infections at the subcutaneous delivery site and provides an opportunity for drug to be diverted for illicit uses. Second, the infusion of large volumes of fluid may result in tissue damage or edema at the site of infusion. In addition, the absorptive capacity of the subcutaneous space limits the volume of fluid that can be delivered, and this volumetric limitation can in turn limit the amount of drug that can be administered.

As an alternative to conventional methods for delivering opioid analgesics, transdermal patch technologies, and controlled release implant technologies have been developed. For example, a fentanyl transdermal patch is commercially available (DURAGESIC®, Janssen Pharmaceutica Products, Titusville, N.J.). The fentanyl patch is provided as a three-day product for pain management applications, and is available in systems containing from 2.5 to 10 mg of the fentanyl agent. Although the product has enjoyed significant commercial success, inherent limitations in the transdermal patch technology employed by the product make it less than ideal as an alternative to conventional systems. Most significantly, the fentanyl patch provides a widely variable rate of fentanyl delivery to the skin over the three-day application period, and there is furthermore a significant variation in the dose of fentanyl delivered among patients. DURAGESIC® Fentanyl Transdermal System Package Insert, 2004. The product is therefore dosage titrated to individual patients on the basis of a nominal flux (the average amount of fentanyl delivered to systemic circulation per hour across average skin) value.

In addition, an implantable osmotic pump sufentanil product is in late-phase clinical testing (CHRONOGESIC®, Durect Corporation, Cupertino, Calif.). The sufentanil pump product is adapted for whole implantation, typically in the subcutaneous space, and thus avoids the delivery variability limitations seen with existing transdermal systems by eliminating the need to traverse the body's skin barrier. The sufentanil pump is currently provided as a three-month product for pain management, and is being tested with systems containing from 9 to 40 mg of the sufentanil agent.

SUMMARY OF THE INVENTION

Transdermal delivery systems for administering sufentanil through the skin are provided. It is thus an object of the present invention to provide a transdermal delivery system for administering sufentanil through the skin, wherein the system provides for a high delivery rate of sufentanil through the skin, with a concomitant low degree of variability in the delivery, wherein the system provides a high degree of system control over delivery of the sufentanil agent.

It is more particularly an object of the invention to provide a transdermal delivery system for administering sufentanil through the skin, where the system provides a dosage form rate control over flux of sufentanil from the system and a net flux from the system through the skin of at least about 1 μg/cm²/hour. The system does not contain a permeation enhancer.

In one aspect of the invention, the dosage form rate control $$\left(\frac{J_N}{J_D}\right)$$

is at least about 50%, in other systems it is at least about 60%, and in still other systems, it is at least about 65% or greater. The dosage form rate control can be provided by a number of different mechanisms/components, either alone or in combination. For example, rate control can be provided at least in part by using a pharmaceutically acceptable adhesive matrix carrier composition. Alternatively, or in addition, a rate controlling membrane can be used to provide control over delivery of sufentanil from the system.

It is another object of the invention to provide a transdermal delivery system for administering sufentanil through the skin. The system is a matrix-type transdermal patch system, and includes a pressure-sensitive adhesive matrix containing the sufentanil agent. The system does not contain a permeation enhancer. The adhesive properties of the matrix are selected such that the system has a shear time of from about 1 to 40 minutes as determined using the Shear Time Measurement Test.

In one aspect of the invention, the adhesive matrix provides dosage form rate control over flux of sufentanil from the system. In other aspects, the system is characterized by having a substantially high net flux sufentanil from the system. In this regard, certain systems provide a net flux of sufentanil from the system through the skin of at least about 1 μg/cm²/hour, while other systems provide a net flux of at least about 1.5 μg/cm²/hour. In certain systems, the overall size of the transdermal delivery system is kept to minimum, such that the adhesive matrix has a drug releasing interface surface area of from about 1-10 cm².

It is still another object of the invention to provide a transdermal delivery system for administering sufentanil through the skin. The system provides a dosage form rate control $$\left(\frac{J_N}{J_D}\right)$$

over flux of sufentanil from the system of at least about 50% while still allowing a net flux of sufentanil from the system through the skin of at least about 1 μg/cm²/hour. The system does not contain a permeation enhancer.

In one aspect of the invention, the dosage form rate control $$\left(\frac{J_N}{J_D}\right)$$

over flux of sufentanil from the system is even higher, for example at least about 60%, while in still other systems the dosage form rate control is at least about 65%. In these systems, the dosage form rate control can be provided by a number of different mechanisms/components, either alone or in combination. Thus, the dosage form rate control can be provided at least in part by using a pharmaceutically acceptable adhesive matrix carrier composition. Alternatively, or in addition, a rate controlling membrane can be used to provide control over delivery of sufentanil from the system. Despite such a high degree of system control in the present systems, certain systems are able to provide a net flux of sufentanil from the system through the skin of at least about 1.5 μg/cm²/hour, while still others can provide a net flux of around 2 μg/cm²/hour, all without the use of a permeation enhancer.

It is a further object of the invention to provide a transdermal delivery system for administering sufentanil through the skin, where the system is able to provide high net flux of sufentanil from the systems without the use of permeation enhancers and where the coefficient of variation in the net flux $$\left(\frac{\Delta J_N}{J_N}\right)$$

is low, being held to about 50% or less. When applied to a subject, the system provides a net flux of sufentanil from the system through the skin of at least about 1 μg/cm²/hour with a very low degree of variability in the net flux from the system, such that the coefficient of variation in the net flux is about 50% or less. The system does not contain a permeation enhancer.

In one aspect of the invention, the low variability system further provides a dosage form rate control over flux of sufentanil form the system. More particularly, certain systems are further able to provide a dosage form rate control $$\left(\frac{J_N}{J_D}\right)$$

over flux of sufentanil from the system of at least about 50% while still providing a very low degree of variability in the net flux from the system. In certain systems, the dosage form rate control $$\left(\frac{J_N}{J_D}\right)$$

over flux of sufentanil from the system is even higher, for example at least about 60%, while in still other systems the dosage form rate control is at least about 65%. The dosage form rate control can be provided by a number of different mechanisms/components, either alone or in combination. Thus, the dosage form rate control can be provided at least in part by using a pharmaceutically acceptable adhesive matrix carrier composition and/or a rate controlling membrane. Despite such a low degree of variability in the net flux from the present systems, certain systems are able to provide an even higher net flux of sufentanil from the system through the skin, on the order of at least about 1.5 μg/cm²/hour, while still others can provide a net flux of around 2 μg/cm²/hour, all without the use of a permeation enhancer.

It is yet a further object of the invention to provide a small sized system that can be used to induce and maintain analgesia for 3 or more days when applied to a subject, where the delivery efficiency at the end of the therapeutic period is at least about 50%, more preferably about 60%, and more preferably 70%, that is, up to about 70% of the sufentanil is delivered to the subject over the course of three days. Accordingly, a transdermal delivery system for administering sufentanil through the skin is provided. The system includes a reservoir containing a sufficient amount of sufentanil to induce and maintain analgesia for 3 or more days when applied to a subject. The reservoir may be an adhesive or non-adhesive matrix, and has a dry, non-hydrated thickness of about 1.25 to 5 mils. The system provides a (drug) delivery efficiency of up to at least about 70% of the sufentanil from the reservoir at the end of 3 or more days of application to a subject.

In one aspect of the invention, the reservoir contains a sufficient amount of sufentanil to induce and maintain analgesia for 5 or more days when applied to a subject while maintaining a delivery efficiency of at least about 70% at the end of the 5 days, and still other systems include a reservoir that contains a sufficient amount of sufentanil to induce and maintain analgesia for 7 or more days when applied to a subject while maintaining a delivery efficiency of at least about 70% at the end of the 7 days. In certain other systems, the delivery efficiency is at least about 80% at the end of the application period. It is preferred that the overall system size of the instant high efficiency transdermal delivery systems is minimized as much as possible. Accordingly, in certain aspects of the invention, the high efficiency systems include a reservoir having a drug releasing interface surface area of from about 1-10 cm². In still further aspects, the high efficiency systems have a substantially small reservoir volume, for example a volume of about 0.2 ml or less. In certain systems, the reservoir has a volume of from about 0.0025 to 0.154 ml.

It is another object of the invention to provide a monolithic transdermal delivery system, where the sufentanil is contained in an adhesive matrix adhered to a backing layer. Accordingly, a monolithic transdermal delivery system for administering sufentanil through the skin is provided. The system includes a pressure-sensitive adhesive matrix that contains sufentanil in an amount above the solubility of sufentanil in the matrix. When the system is applied to a subject, the system provides a substantially constant steady state net flux of sufentanil from the system through the skin of at least about 1 μg/cm²/hour for at least about 24 hours. The system does not include a permeation enhancer or rate controlling membrane. It is a feature of the invention that the systems are able to provide such high net flux systems that do not employ a permeation enhancer or rate controlling membrane and can still perform to such high standards, where upon achieving steady state conditions, the system provides, at least a first order release rate profile such that the system achieves substantially zero order release to provide a constant steady state flux of sufentanil from the system over an extended period of time. In certain systems, the system provides a substantially constant steady state net flux of sufentanil from the system through the skin of at least about 1 μg/cm²/hour for at least about 36 hours.

In one aspect of the invention, certain systems are also able to provide an even higher steady state net flux net flux of sufentanil from the system through the skin, for example at least about 1.5 μg/cm²/hour in some systems, or even around 2 μg/cm²/hour in other systems. In certain systems, the overall size of the transdermal delivery system is kept to minimum, such that the adhesive matrix has a drug releasing interface surface area of from about 1-10 cm².

It is a still further object of the invention to provide a monolithic transdermal delivery system for administering sufentanil through the skin. The system includes a pressure-sensitive adhesive matrix that contains sufentanil in an amount above the solubility of sufentanil in the matrix. When the system is applied to a subject, the system provides a net flux of sufentanil from the system through the skin of at least about 1 μg/cm²/hour. The system provides a dosage form rate control over flux of sufentanil from the system, but the system does not include a permeation enhancer or rate controlling membrane. In these systems, the sufentanil is provided as a depot, and is thus present in the system in an amount above the solubility of sufentanil in the system, such that there will be both dissolved and undissolved sufentanil in the system.

In one aspect of the invention, the dosage form rate control $$\left(\frac{J_N}{J_D}\right)$$

over flux of sufentanil from the system is at least about 50% while still providing the substantially high rate of net flux from the system. In certain systems, the dosage form rate control $$\left(\frac{J_N}{J_D}\right)$$

over flux of sufentanil from the system is even higher, for example at least about 60%, while in still other systems the dosage form rate control is at least about 65%. The dosage form rate control can be provided by a number of different mechanisms/components, either alone or in combination. Thus, the dosage form rate control can be provided at least in part by using a pharmaceutically acceptable adhesive matrix carrier composition and/or a rate controlling membrane. Despite not including a permeation enhancer or rate controlling membrane, certain systems are able to provide an even higher net flux of sufentanil from the system through the skin, on the order of at least about 1.5 µg/cm$^2$/hour, while still others can provide a net flux of around 2 µg/cm$^2$/hour.

It is a still further object of the invention to provide a transdermal delivery system for administering sufentanil through the skin of a living subject, wherein the system provides a substantially constant delivery rate of sufentanil over a single application administration period of at least about 48 hours and the constant delivery rate is sufficient to establish and maintain a plasma sufentanil concentration having a maximum to minimum ratio of about 1.8 or less over the relevant administration period.

In one aspect of the invention, the delivery rate of sufentanil from the transdermal delivery system is substantially zero order. In other aspects of the invention, the delivery rate of sufentanil is characterized by a total decline or increase of about 5 to 6% over the administration period, and preferably, the delivery rate of sufentanil is characterized by substantially no total increase or decrease over the administration period. The subject transdermal delivery systems are able to provide a delivery rate at steady state of at least about 1 µg/hr to 10 µg/hr, and the administration period is at least about 48 hours to 7 days. In certain embodiments, the net flux from the system through the skin is at least about 1 µg/cm$^2$/hour, and the system does not contain a permeation enhancer. In other aspects of the invention, the system has a shear time of from about 1 to 40 minutes as determined using the Shear Time Measurement test. In still further aspects, the system provides dosage form rate control ($J_N/J_D$) over flux of sufentanil from the system of at least about 50% and a net flux from the system through the skin of at least about 1 µg/cm$^2$/hour. In other aspects, the system provides a net flux of sufentanil from the system through the skin of at least about 1 µg/cm$^2$/hour with a coefficient of variation ($\Delta J_N/J_N$) of about 50% or less, or the system is a monolithic system comprising a pressure-sensitive adhesive matrix containing sufentanil in an amount above the solubility of sufentanil in the matrix, and the subject system provides a substantially constant steady state net flux of sufentanil from the system through the skin of at least about 1 µg/cm$^2$/hour for at least about 24 hours. In yet other aspects, system is a monolithic system including a pressure-sensitive adhesive matrix containing the sufentanil active agent in an amount above the solubility of sufentanil in the matrix, and the system provides a net flux from the system through the skin of at least about 1 µg/cm$^2$/hour, wherein a dosage form control over flux of sufentanil from the system is provided by the system itself. Preferably, the above-described systems do not include a permeation enhancer or a rate controlling membrane.

It is an advantage of the present invention that the transdermal delivery systems are able to provide sustained analgesia in a subject for from 3 to 7 days. It is a further advantage of the invention that the systems are readily constructed to provide any number of different dosages and sizes, and further are able provide preferential pharmacological release characteristics and profiles. It is a still further advantage of the invention that the system control provided by the systems allows for maximum control over the plasma concentrations of the delivered sufentanil, and therefore the therapeutic effect.

These and other objects, aspects and advantages of the present invention will readily occur to the skilled practitioner upon reading the instant disclosure and specification.

DETAILED DESCRIPTION OF THE INVENTION

Figure 1:
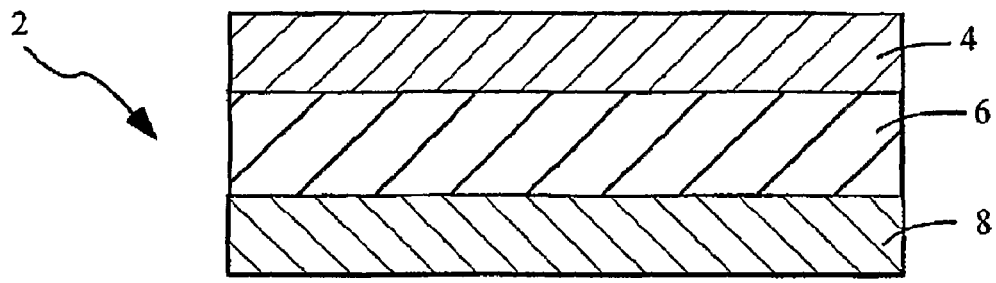
FIG. 1 presents a cross-sectional view through a transdermal delivery system according to the present invention.

Before describing the present invention in detail, it is to be understood that this invention is not limited to particularly exemplified materials or process parameters as such may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

It must be noted that, as used in this specification and the appended claims, the singular forms "a," "an" and "the" include plural referents unless the content clearly dictates otherwise. Thus, for example, reference to "a polymer"

includes a mixture of two or more such molecules, reference to "a solvent" includes a mixture of two or more such compositions, reference to "an adhesive" includes mixtures of two or more such materials, and the like. In addition, whenever a specified range is provided in the instant specification and claims, use of the modifier "about" is applied to all values or quantities specified by that range. Thus, the phrase "about 1-12 wt %" means "about 1 to about 12 wt %", and the phrase "about 1-10 cm$^2$" means "about 1 to about 10 cm$^2$", and the like.

It is an object of the present invention to provide a transdermal delivery system for administering sufentanil through the skin.

A transdermal delivery system for administering sufentanil through the skin was first suggested 1984 in U.S. Pat. No. 4,588,580 to Gale et al. The Gale et al. patent claims the transdermal patch technology employed in the commercial DURAGESIC® fentanyl transdermal patch product. Over the course of the next twenty years, literally thousands of other patent applications have been filed relating to a wide spectrum of transdermal delivery technologies, transdermal patch design and components, and transdermal delivery techniques. A large number of these new patent applications have, like the Gale et al. patent, included the suggestion for a sufentanil patch, but these suggestions are provided by way of including the sufentanil agent in a long laundry list of drugs rather than by providing an enabling disclosure of how to actually design a proper sufentanil system. However, despite twenty years of such suggestions, there has never been a sufentanil patch that has entered into clinical testing.

The glaring absence of sufentanil transdermal systems from the pharmaceutical research and development and clinical landscapes, despite both the commercial success of a fentanyl patch and constant suggestions from the patent literature, can be attributed to a number of features related to transdermal delivery in general and the sufentanil agent in specific, all of which features are well recognized in the transdermal art. Initially, all transdermal delivery systems must overcome the natural barrier to percutaneous absorption of an agent, which barrier function is naturally provided by the skin. The physical and chemical properties of any particular agent affect the degree to which that agent may move across the skin barrier (the epidermis) via percutaneous absorption, and thus agents can be characterized by their skin permeation or epidermal permeability. Agents exhibiting a high degree of skin permeation are good candidates for transdermal delivery systems, whereas agents exhibiting a low degree of skin permeation are generally considered not to be good candidates.

There is also a very high degree of variability in the permeability of human skin to any particular agent. In fact, skin permeability is known to differ widely by region (e.g., skin from the thigh will have different permeability than skin from the chest, and both will differ from skin from the arm), by individual (e.g., the skin from different individuals will have different permeability), and even by specific site within the same region (e.g., skin from different sites on a particular individual's forearm will have different permeability). Shaw et al. (1991) in *Physiology, Biochemistry, and Molecular Biology of the Skin*, Second Ed., pp. 1447-1479, Goldsmith, L. A. Ed., Oxford University Press, Oxford, UK. These variances are reported to be as much as 70%. Accordingly, it is not just a matter of overcoming the skin barrier, rather transdermal delivery system designs must also account for a wide variance in the degree to which an agent is able to traverse the skin.

Another inherent feature in transdermal delivery systems relates to the relationship between the skin surface area that the system releases the agent to (the target surface or drug releasing interface) and the amount agent that can be delivered from the system. Transdermal delivery systems must maintain intimate contact with the target surface for the duration of treatment. Accordingly, there is a de facto upward limit on the size for any transdermal system dictated by the size where a given patch will be prone to lifting and peeling from the target surface in response to normal flexing and movement by the individual. A reasonable transdermal patch size generally has a drug releasing interface surface area of around 40 cm$^2$ or less. However, restricting the size of a transdermal delivery system in this manner limits the amount of agent that can be delivered from that system. Accordingly, agents with poor skin permeability generally require larger patch sizes to bring agent delivery rates up to acceptable levels.

With regard to the features of the sufentanil agent itself, it is well known that sufentanil has a very high potency, reported to be from 7.5-15 times more potent than fentanyl. See U.S. Pat. No. 4,588,580 to Gale et al. Sufentanil also has a relatively narrow therapeutic index and, due to its very high potency, will produce highly undesirable side effects upon over dosage that can lead to death. Sufentanil is also reported to have extremely poor skin permeability, for example in the Gale et al. patent it was noted that fentanyl has poor skin permeability and that sufentanil has even less permeability than fentanyl, and in U.S. Patent Publication No. US 2003/0026829 to Venkatraman et al., it was noted that sufentanil is from 50 to 75% less permeable than fentanyl in skin. Accordingly, the skilled transdermal artisan is faced with conflicting choices when considering the design of a sufentanil transdermal delivery system. It would be expected that the amount of sufentanil that can be delivered from a given system will be exceedingly low due to the poor skin permeability of sufentanil. This in turn suggests that techniques must be employed to increase sufentanil skin permeability, for example by using permeation enhancers to increase delivery to a sufficient rate to fit within the narrow therapeutic index for sufentanil. However, the side effect profile for sufentanil suggests just the opposite, where the possibility of overdose would lead to design of a system that has a restricted delivery rate.

When the above-noted sufentanil-specific design considerations are combined with considerations such as the need to reduce the affect of skin variability on transdermal delivery system performance, it is no small wonder that an effective sufentanil transdermal delivery system has heretofore not been developed. The skilled artisan was left with the design concerns discussed above and two suggested approaches for a transdermal sufentanil system, appearing at either end of a two-decade long period and providing two similar approaches to the problem. The first suggestion for a sufentanil system was provided in U.S. Pat. No. 4,588,580 to Gale et al. In this document, Gale et al. noted the low skin permeability of both fentanyl and sufentanil. The two suggestions for system design that were provided by Gale et al. were to either provide a matrix type system that delivered the agent for continuous periods and had no system control (relying instead on skin permeability to control agent input rates), or preferably to provide a system, where the system itself controls the maximum rate at which the agent is delivered through the skin. In the second design that provides system control, Gale et al. taught that it is necessary to substantially increase the flux of the agent (fentanyl or sufentanil) through the skin by use of a skin permeation enhancer. The second suggestion from Gale et al. was used to design the DURAGESIC® transdermal fentanyl system, where a reservoir of the fentanyl agent is provided with a rate-limiting membrane to provide a system-controlled patch. Alcohol is added to the reservoir as a permeation enhancer, where the alcohol serves to enhance fentanyl flux through the rate-limiting membrane and increase the permeability of the skin to fentanyl. This selected design provides a transdermal delivery system that is able to deliver the fentanyl agent at acceptably high rates (due to the addition of a permeation enhancer), but net delivery is still highly variable, particularly from an interindividual perspective (DURAGESIC® Fentanyl Transdermal System Package Insert, 2004). Whereas such person-to-person variability may be acceptable in a fentanyl system, it would likely not be acceptable in a sufentanil system due to safety considerations. The other alternative suggested by Gale et al., that is, a system that relies solely on skin permeability to control delivery rates, would likewise have unacceptably high variability for a sufentanil system.

The second suggested approach for a sufentanil transdermal delivery system was provided almost 20 years after Gale et al. in U.S. Patent Publication No. US 2003/0026829 to Venkatraman et al. In this document, Venkatraman et al. noted the low skin permeability of both fentanyl and sufentanil, and in particular reported that sufentanil has from 50 to 75% less skin permeability than fentanyl. It was also noted that the fentanyl and sufentanil agents required careful handling due to their safety profiles. The system design that is suggested for sufentanil uses a subsaturated system (where the sufentanil agent is present in an amount below the solubility limit of the agent in the selected system) monolithic matrix, wherein the system is not rate-controlled. Accordingly, the Venkatraman et al. transdermal system would be expected to administer the sufentanil agent at a decreasing rate that is proportional to the level of saturation of the agent in the system, and relies upon skin permeability to control the delivery rate. This approach is generally the first approach suggested by Gale et al., that is, a non-rate controlled system. Venkatraman et al. teach that a saturated system (e.g., depot system) would provide for a higher rate of delivery, but that their subsaturated system must nevertheless be selected. A review of in vitro data relating to delivery of sufentanil from the Venkatraman et al. system indicates that it provides a low net flux (for systems containing between 2-11% sufentanil, the net flux ranges from 0.1 to 0.9 μg/cm²/hour), and further that there is substantial variability in the net delivery. Here again, it is believed that whereas such variability may be suitable for a fentanyl transdermal system, it would not be suitable for a sufentanil transdermal delivery system.

Applicant has taken a substantial departure from these past suggested approaches, and has now developed a transdermal delivery system for administering sufentanil through the skin, where the system is characterized by having a high degree of system control (dosage form rate control) over delivery of sufentanil from the system in spite of also having a high total net flux from the system through the skin with a particularly low variability (coefficient of variation). The present delivery systems are surprisingly able to provide these performance features without the use of permeation enhancers.

From Shaw et al. (1985) "Transdermal Dosage Forms," in *Rate Control in Drug Therapy*, (Prescott et al. eds), pp: 65-70, Churchill Livingstone, Edinburgh, it is known that in a rate controlled transdermal delivery system, the relation between the net flux ($J_N$), the flux through skin ($J_S$) and flux from the dosage form ($J_D$) can be given by the following equation:

$$\frac{1}{J_N} = \frac{1}{J_S} + \frac{1}{J_D} \quad \text{(Formula I)}$$

The relationship between the variability in net flux through the skin from the dosage form $$\frac{\Delta J_N}{J_N},$$

the variability in skin flux $$\frac{\Delta J_S}{J_S},$$

to the degree of dosage form rate control provided by the system, which is defined as $$\frac{J_N}{J_D},$$

can be represented by the following equation:

$$\frac{\Delta J_N}{J_N} = \frac{\Delta J_S}{J_S}\left(1 - \frac{J_N}{J_D}\right). \quad \text{(Formula II)}$$

As can be seen from the relationships represented by Formula I and Formula II, the ability to exert a high degree of dosage form rate control in a transdermal delivery system can substantially eliminate the effect that skin flux variability may have on the variability of net flux through the skin from the dosage form. The transdermal delivery systems of the present invention are designed to provide a high degree of dosage form rate control. Accordingly, in one embodiment of the invention, a transdermal delivery system for administering sufentanil through the skin is provided. The system provides a dosage form rate control over flux of sufentanil from the system and a net flux from the system through the skin of at least about 1 μg/cm²/hour. The system does not contain a permeation enhancer. In particular systems of the invention, the dosage form rate control $$\left(\frac{J_N}{J_D}\right)$$

is at least about 50%, in other systems it is at least about 60%, and in still other systems, it is at least about 65% or greater. The dosage form rate control can be provided by a number of different mechanisms/components, either alone or in combination. For example, rate control can be provided at least in part by using a pharmaceutically acceptable adhesive matrix carrier composition, wherein the materials used to construct the matrix are selected so as to provide control over delivery of the sufentanil agent from the transdermal delivery system. Alternatively, or in addition, a rate controlling membrane can be used to provide control over delivery of sufentanil from the system.

In the instant transdermal delivery systems, the sufentanil agent can be present in the system in an amount of about 1-20 weight percent (wt %) relative to the total system, preferably in an amount of about 1-20 wt %, preferably in an amount of about 1-12 wt %. In certain systems, the sufentanil is provided as a depot, and is thus present in the system in an amount above the solubility of sufentanil in the system, such that there will be both dissolved and undissolved sufentanil in the system. In any regard, the transdermal delivery systems are provided with sufficient amount of the sufentanil agent to provide for a steady state net flux sufficient to administer the sufentanil at from about 0.01 to 200 μg/hour when the system is applied to the skin of subject. Certain other systems of the present invention provide a steady state net flux sufficient to administer sufentanil at from about 1 to 20 μg/hour when the system is applied to the skin of a subject, while still further systems are able to provide a steady state net flux sufficient to administer sufentanil at from about 1 to 2 μg/hour.

The present transdermal delivery systems contain a sufficient amount of sufentanil so that they may be used to induce and maintain a suitable state of analgesia in a subject for 3 or more days when applied to the skin of that subject. Other systems contain a sufficient amount of sufentanil to induce and maintain a suitable state of analgesia in a subject for 5 or more days, while still others contain enough to induce and maintain a suitable state of analgesia in a subject for 7 or more days.

The long duration intended uses of the present transdermal delivery systems impart further design considerations upon those systems. Particularly, the transdermal delivery systems must maintain intimate contact with the target surface (drug releasing interface surface) for the duration of treatment. A system that has insufficient adhesive properties and/or which is too rigid and nonflexible, will be prone to displacement from the target skin surface, thereby interrupting or at least reducing the intended rate of delivery of sufentanil from the system. A patch that is too large will also be prone to lifting and peeling from the target surface in response to normal flexing and movement by the individual. In addition, the adhesive properties of the system must take into account the changes in skin hydration brought about by normal daily activity, such as bathing or showering, and perspiring due to exercise or exertion.

Accordingly, the materials used in the construction of a transdermal delivery system according to the present invention are selected to provide a patch that has suitable drape, that is, flexibility so as to maintain contact between the target skin surface and the drug releasing interface of the system throughout normal movement, stretching and bending of the skin site. In those transdermal delivery systems that are provided as a monolithic, matrix-type system (where the sufentanil is blended with an adhesive carrier composition, such as a pressure-sensitive adhesive, to provide both a carrier matrix for the sufentanil as well as the means for affixing the system to the target skin surface), the adhesive is selected to have a shear time within a specified range of times deemed suitable for present systems.

More particularly, a Shear Time Measurement Test can be used to assess adhesive properties in a monolithic transdermal delivery system constructed according to the present invention. The Shear Time Measurement Test is conducted as follows. A bar formed from steel plate is provided. The bar is placed on a horizontal surface and the face of the bar is cleaned using an appropriate alcohol wipe (typically three times using methanol) and dried. A sample transdermal patch is provided having a ½" width. A first end of the sample patch is applied to the cleaned surface of the bar so that the contact with the bar is ½"×½" (the sample is applied to the surface ½" from the bottom of the bar). The second end of the sample patch hangs freely below the bar. A weight holder is attached to the free end of the sample patch. The bar is then suspended at a suitable height using a support structure, such that the face of the bar with the patch adhered to it is completely vertical. Care is taken not to impart any peeling force on the sample patch during this set-up procedure. The test is then run by carefully attaching a 100 g weight to the weight holder at the free end of the sample patch and recording the time that it takes for the sample patch to completely separate from the face of the vertical test bar. An appropriate shear time as determined by the Shear Time Measurement Test indicates that a sample adhesive system has suitable skin adhesion properties and suitable cold flow properties. A passing test result from the Shear Time Measurement Test is between about 1 to 40 minutes. Patches that adhere for longer periods of time will generally adhere too tightly to the skin surface, giving rise to displacement under influence of normal movement. Patches that adhere for shorter periods of time will not have suitable adherence to remain in place. In preferred embodiments, the adhesive system should have a Shear Time Measurement Test result of between about 2 and 20 minutes, and more preferably between about 5 and 15 minutes.

Accordingly, in an embodiment of the invention, a transdermal delivery system for administering sufentanil through the skin is provided. The system is a matrix-type transdermal patch system, and includes a pressure-sensitive adhesive matrix containing the sufentanil agent. The system does not contain a permeation enhancer. The adhesive properties of the matrix are selected such that the system has a shear time of from about 1 to 40 minutes as determined using the Shear Time Measurement Test. In the subject system, the adhesive matrix provides dosage form rate control over flux of sufentanil from the system. The systems are characterized by having a substantially high net flux of sufentanil from the system. In this regard, certain systems provide a net flux of sufentanil from the system through the skin of at least about 1 $\mu g/cm^2$/hour, while other systems provide a net flux of at least about 1.5 $\mu g/cm^2$/hour. In certain preferred systems, the overall size of the transdermal delivery system is kept to minimum, such that the adhesive matrix has a drug releasing interface surface area of from about 1-10 $cm^2$. In certain systems, the sufentanil agent can be present in an amount of about 1-20 weight percent (wt %) relative to the total system, preferably in an amount of about 1-12 wt %. In certain other systems, the sufentanil is provided as a depot, and is thus present in the system in an amount above the solubility of sufentanil in the system, such that there will be both dissolved and undissolved sufentanil in the system. The transdermal delivery systems are provided with sufficient amount of the sufentanil agent to provide for a steady state net flux sufficient to administer the sufentanil at from about 0.01 to 200 μg/hour when the system is applied to the skin of a subject. Certain other systems of the present invention provide a steady state net flux sufficient to administer sufentanil at from about 1 to 20 μg/hour when the system is applied to the skin of a subject, while still further systems are able to provide a steady state net flux sufficient to administer sufentanil at from about 1 to 2 μg/hour.

The present adhesive transdermal delivery systems contain a sufficient amount of sufentanil so that they may be used to induce and maintain a suitable state of analgesia in a subject for 3 or more days when applied to the skin of that subject. Other systems contain a sufficient amount of sufentanil to induce and maintain a suitable state of analgesia in a subject for 5 or more days, while still others contain enough to induce and maintain a suitable state of analgesia in a subject for 7 or more days.

In one particular embodiment, the instant adhesive transdermal delivery systems are provided as a dimensionally stratified family of transdermal patches of varying doses, all having an adhesive matrix with a drug releasing interface surface area of from about 1-10 cm². For example, the family can include four patches having drug releasing interface surface area of 2, 4, 6 and 8 cm², respectively, wherein the patches respectively contain 1, 2, 3 and 4 mg of the sufentanil agent. In this case, the size of the patch provides a visual clue to a health service provider, possibly avoiding accidental application of a transdermal delivery system containing an incorrect dose of sufentanil. In addition, the nested doses allow for convenient dosing of an individual, where step-wise incremental increases/decreases in the dose can be made with the simple application/removal of one or more of the sized patches in the family. The superior adhesive properties displayed by the instant adhesive systems further allow for in-clinic dose reduction procedures, where a particular patch (e.g., the 8 cm² patch containing 4 mg of sufentanil) can be divided into halves, thirds or quarters, to provide a different, fully operable patch having a reduced size and therefore a reduced dose of sufentanil (e.g., a 4 cm² patch with 2 mg sufentanil, or a 2 cm² patch with 1 mg sufentanil). In this regard, indicia may be provided on the backing of the subject patches to facilitate accurate division of a particular patch into two or more patches of smaller size and dose.

It is a surprising feature of the transdermal delivery systems of the present invention that they are able to provide such high system control and high net flux of sufentanil from the systems without the use of permeation enhancers. It is even more surprising that transdermal delivery systems displaying such high system control and net flux of sufentanil can be provided in such small sizes, generally in the order of about 20% the size of previous transdermal systems. Accordingly, in one embodiment, a transdermal delivery system for administering sufentanil through the skin is provided. The system provides a dosage form rate control $$\left(\frac{J_N}{J_D}\right)$$

over flux of sufentanil from the system of at least about 50% while still allowing a net flux of sufentanil from the system through the skin of at least about 1 μg/cm²/hour. The system does not contain a permeation enhancer. In certain systems, the dosage form rate control $$\left(\frac{J_N}{J_D}\right)$$

over flux of sufentanil from the system is even higher, for example at least about 60%, while in still other systems the dosage form rate control is at least about 65%. As with the other systems of the present invention, the dosage form rate control can be provided by a number of different mechanisms/components, either alone or in combination. Thus, the dosage form rate control can be provided at least in part by using a pharmaceutically acceptable adhesive matrix carrier composition, wherein the materials used to construct the matrix are selected so as to provide control over delivery of the sufentanil agent from the transdermal delivery system.

Alternatively, or in addition, a rate controlling membrane can be used to provide control over delivery of sufentanil from the system. Despite such a high degree of system control in the present systems, certain systems are able to provide a net flux of sufentanil from the system through the skin of at least about 1.5 μg/cm²/hour, while still others can provide a net flux of around 2 μg/cm²/hour, all without the use of a permeation enhancer.

In certain high system control/high net flux systems, the sufentanil agent can be present in an amount of about 1-20 weight percent (wt %) relative to the total system, preferably in an amount of about 1-12 wt %. In certain other systems, the sufentanil is provided as a depot, and is thus present in the system in an amount above the solubility of sufentanil in the system, such that there will be both dissolved and undissolved sufentanil in the system. The transdermal delivery systems are provided with sufficient amount of the sufentanil agent to provide for a steady state net flux sufficient to administer the sufentanil at from about 0.01 to 200 μg/hour when the system is applied to the skin of a subject. Certain other systems of the present invention provide a steady state net flux sufficient to administer sufentanil at from about 1 to 20 μg/hour when the system is applied to the skin of a subject, while still further systems are able to provide a steady state net flux sufficient to administer sufentanil at from about 1 to 2 μg/hour.

The present high system control/high net flux transdermal delivery systems contain a sufficient amount of sufentanil so that they may be used to induce and maintain a suitable state of analgesia in a subject for 3 or more days when applied to the skin of that subject. Other systems contain a sufficient amount of sufentanil to induce and maintain a suitable state of analgesia in a subject for 5 or more days, while still others contain enough to induce and maintain a suitable state of analgesia in a subject for 7 or more days.

It is another surprising feature of the transdermal delivery systems of the present invention that they are able to provide such high net flux of sufentanil from the systems without the use of permeation enhancers, wherein the coefficient of variation in the net flux $$\left(\frac{\Delta J_N}{J_N}\right)$$

is low, being held to about 50% or less. It is even more surprising that transdermal delivery systems displaying such high net flux of sufentanil and such low variability in the net flux can be provided in such small sizes, generally in the order of about 20% the size of previous transdermal systems. Accordingly, in one embodiment, a transdermal delivery system for administering sufentanil through the skin is provided. When applied to a subject, the system provides a net flux of sufentanil from the system through the skin of at least about 1 μg/cm²/hour with a very low degree of variability in the net flux from the system, such that the coefficient of variation in the net flux $$\left(\frac{\Delta J_N}{J_N}\right)$$

is about 50% or less. The system does not contain a permeation enhancer.

In certain preferred low variability systems, the subject system further provides a dosage form rate control over flux of sufentanil form the system. More particularly, certain systems are further able to provide a dosage form rate control $$\left(\frac{J_N}{J_D}\right)$$

over flux of sufentanil from the system of at least about 50% while still providing a very low degree of variability in the net flux from the system. In certain systems, the dosage form rate control $$\left(\frac{J_N}{J_D}\right)$$

over flux of sufentanil from the system is even higher, for example at least about 60%, while in still other systems the dosage form rate control is at least about 65%. As with the other systems of the present invention, the dosage form rate control can be provided by a number of different mechanisms/components, either alone or in combination. Thus, the dosage form rate control can be provided at least in part by using a pharmaceutically acceptable adhesive matrix carrier composition and/or a rate controlling membrane. Despite such a low degree of variability in the net flux from the present systems, certain systems area able to provide an even higher net flux of sufentanil from the system through the skin, on the order of at least about 1.5 μg/cm²/hour, while still others can provide a net flux of around 2 μg/cm²/hour, all without the use of a permeation enhancer.

In certain low variability/high net flux systems, the sufentanil agent can be present in an amount of about 1-20 weight percent (wt %) relative to the total system, preferably in an amount of about 1-12 wt %. In certain other systems, the sufentanil is provided as a depot, and is thus present in the system in an amount above the solubility of sufentanil in the system, such that there will be both dissolved and undissolved sufentanil in the system. The transdermal delivery systems are provided with sufficient amount of the sufentanil agent to provide for a steady state net flux sufficient to administer the sufentanil at from about 0.01 to 200 μg/hour when the system is applied to the skin of a subject. Certain other systems of the present invention provide a steady state net flux sufficient to administer sufentanil at from about 1 to 20 μg/hour when the system is applied to the skin of a subject, while still further systems are able to provide a steady state net flux sufficient to administer sufentanil at from about 1 to 2 μg/hour.

The present low variability/high net flux transdermal delivery systems contain a sufficient amount of sufentanil so that they may be used to induce and maintain a suitable state of analgesia in a subject for 3 or more days when applied to the skin of that subject. Other systems contain a sufficient amount of sufentanil to induce and maintain a suitable state of analgesia in a subject for 5 or more days, while still others contain enough to induce and maintain a suitable state of analgesia in a subject for 7 or more days.

It is still another surprising feature of the transdermal delivery systems of the present invention that a very small sized system can be used to induce and maintain analgesia for 3 or more days when applied to a subject, wherein the delivery efficiency at the end of the therapeutic period is at least about 70%, that is, at least about 70% of the sufentanil is delivered to the subject over the course of three days. The delivery efficiency, or system efficiency, for a given transdermal delivery system at any point in time can be assessed by dividing the mass of sufentanil delivered from the system at substantially zero order by the total mass of sufentanil that was provided in the system at the initiation of the administration. In addition, since the mass of sufentanil provided in a new system is known, the delivery efficiency for a given patch removed from a subject after, e.g., a three day administration period, can be readily determined by extracting the sufentanil remaining in the system to determine the remaining mass of sufentanil and then comparing this mass against the starting mass. In the present invention, the transdermal delivery systems are designed such that the sufentanil has a very low solubility in the system, the thickness of the reservoir in which the sufentanil is provided is kept to a minimum, and the overall system size is minimized as much as possible. In addition, other controls over system efficiency can be used, such as where the sufentanil is added to a system in a tightly controlled particle size distribution.

Accordingly, in one embodiment, a transdermal delivery system for administering sufentanil through the skin is provided. The system includes a reservoir containing a sufficient amount of sufentanil to induce and maintain analgesia for 3 or more days when applied to a subject. The reservoir may be an adhesive or non-adhesive matrix, and has a dry, non-hydrated thickness of about 1.25 to 5 mils. The system provides a delivery efficiency of at least about 50% of the sufentanil from the reservoir at the end of 3 or more days of application to a subject, preferably at least about 60%, and more preferably at least about 70%. In certain systems, the reservoir contains a sufficient amount of sufentanil to induce and maintain analgesia for 5 or more days when applied to a subject while maintaining a delivery efficiency of up to at least about 70% at the end of the 5 days, and still other systems include a reservoir that contains a sufficient amount of sufentanil to induce and maintain analgesia for 7 or more days when applied to a subject while maintaining a delivery efficiency of up to at least about 70% at the end of the 7 days. In certain other systems, the delivery efficiency is even greater, for example, at least about 80% at the end of the application period. It is preferred that the overall system size of the instant high efficiency transdermal delivery systems is minimized as much as possible. Accordingly, in preferred embodiments, the high efficiency systems include a reservoir having a drug releasing interface surface area of from about 1-10 cm². In still further preferred embodiments, the high efficiency systems have a substantially small reservoir volume, for example a volume of about 0.2 ml or less. In certain systems, the reservoir has a volume of from about 0.0025 to 0.154 ml.

In certain systems, the reservoir in the high efficiency transdermal delivery systems includes an adhesive matrix composition. In certain preferred systems, the subject system further provides a dosage form rate control over flux of sufentanil form the system. More particularly, certain systems are further able to provide a dosage form rate control $$\left(\frac{J_N}{J_D}\right)$$

over flux of sufentanil from the system of at least about 50% while still providing a high delivery efficiency from the system. In certain systems, the dosage form rate control $$\left(\frac{J_N}{J_D}\right)$$

over flux of sufentanil from the system is even higher, for example at least about 60%, while in still other systems the dosage form rate control is at least about 65%. As with the other systems of the present invention, the dosage form rate control can be provided by a number of different mechanisms/components, either alone or in combination. Thus, the dosage form rate control can be provided at least in part by using a pharmaceutically acceptable adhesive matrix carrier composition and/or a rate controlling membrane. Additionally, certain other high efficiency systems are also able to provide a relatively high net flux of sufentanil from the system through the skin, for example at least about 1 µg/cm$^2$/hour in some systems, and at least about 1.5 µg/cm$^2$/hour, or even around 2 µg/cm$^2$/hour in other systems. It is notable that in these high efficiency/high flux systems, there is still no need to provide a permeation enhancer, and as such, certain of the instant systems do not include a permeation enhancer.

In certain of the instant high efficiency transdermal delivery systems of the present invention, the sufentanil agent can be present in an amount of about 1-20 weight percent (wt %) relative to the total system, preferably in an amount of about 1-12 wt %. In certain other systems, the sufentanil is provided as a depot, and is thus present in the system in an amount above the solubility of sufentanil in the system, such that there will be both dissolved and undissolved sufentanil in the system. The transdermal delivery systems are provided with sufficient amount of the sufentanil agent to provide for a steady state net flux sufficient to administer the sufentanil at from about 0.01 to 200 µg/hour when the system is applied to the skin of a subject. Still other systems of the present invention provide a steady state net flux sufficient to administer sufentanil at from about 1 to 20 µg/hour when the system is applied to the skin of a subject, while further systems are able to provide a steady state net flux sufficient to administer sufentanil at from about 1 to 2 µg/hour.

Figure 2:
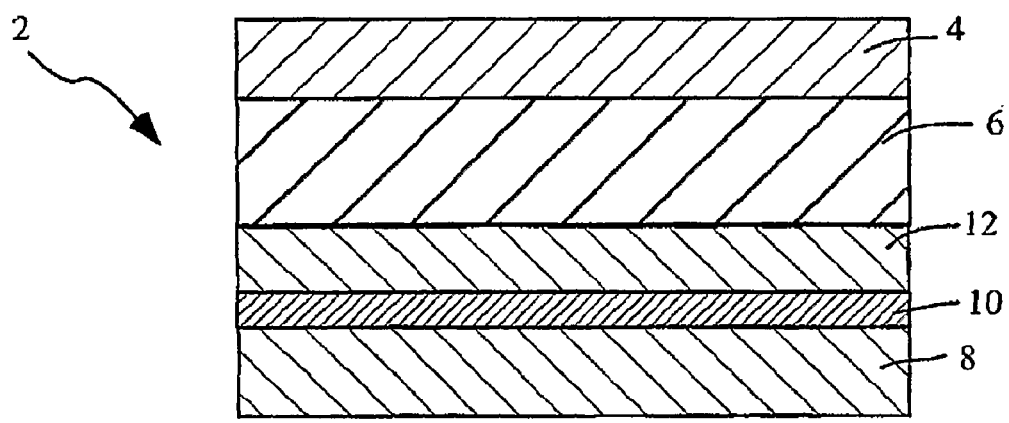
FIG. 2 presents a cross-sectional view through another transdermal delivery system according to the present invention.

The transdermal delivery systems of the invention may be provided as either a liquid or gel reservoir-type or a matrix-type device. Both of these configurations will naturally include a backing layer that provides a protective outer surface for the devices, as well as a release liner or layer that will cover the adhesive portion of the device that is used to affix the same to the skin of a subject. The release liner is removed prior to application, thereby exposing the adhesive portion of the device, which will typically be a pressure-sensitive adhesive. Accordingly, referring to FIGS. 1 and 2, a transdermal patch device is generally indicated at 2. The device includes a backing layer 4, a reservoir 6 that contains the sufentanil agent, and a release liner 8. The reservoir 6 may be a liquid or gel reservoir, or it may be a matrix carrier that can be self-adhesive or non-adhesive. Referring specifically to FIG. 2, in those devices where the reservoir is either a liquid or gel reservoir, or a non-adhesive matrix, the device 2 will further comprise an adhesive layer 10 that serves to adhere the device to the skin. The adhesive layer 10 is generally a drug-permeable adhesive that is applied over the reservoir. In some devices, a further layer 12 can be employed as a rate controlling membrane, where the layer is selected to provide for selective movement of the sufentanil agent through the layer.

The backing layer 4, which adheres to the drug-containing reservoir 6 serves as the upper layer of the device during use and functions as the primary structural element of the device. The backing layer is thus typically a sheet or film of a preferably flexible elastomeric material that is substantially impermeable to the sufentanil agent. This backing layer 4 typically has a thickness of about 0.1 to 5 mils, preferably about 0.5 to 2 mils, and more preferably about 1 to 1.5 mils, and is generally a material that permits the device to follow the contours of the skin such that it can be worn comfortably on any skin area including joints or other areas of flexure. Accordingly, there is a reduced likelihood of the device dislodging from the skin due to differences in the flexibility or resiliency of the skin and the device, as well as in response to normal mechanical strain brought about by movement and the like. The backing layer may further be a monolithic (single layer) or a multi-layer (multilaminate), and may further be a breathable or occlusive material comprising fabric. Most commonly, the backing layer 4 will be a polymeric material, or a laminate of polymeric materials. Suitable materials include, but are not limited to, polyethylene, polypropylene, polyesters, polyurethanes, polyethylene vinyl acetate, polyvinylidene chloride, block copolymers such as PEBAX, polyvinyl acetate, polyvinylidene chloride, polyurethane, ethylene vinyl acetate, polyethylene terephthalate, polybutylene terephthalate, coated paper products, metal or metalized sheets and the like, and any combinations thereof.

In preferred embodiments, the backing layer 4 comprises a low-, medium- or high-density polyethylene material, or a polyester material. In a particularly preferred embodiment, the backing layer comprises a laminate of polyethylene and aluminum vapor coated polyester (e.g., SCOTCHPAK® 1109 Backing, available from 3M, St. Paul, Minn.), or a laminate of polyester and polyethylene/ethylene vinyl acetate (e.g., SCOTCHPAK® 9733 Backing, available from 3M).

The reservoir 6 is disposed on the backing layer. The reservoir may be formed from any number of standard materials well known in the art. In those devices where the reservoir is a liquid or gel-type reservoir, any suitable gelling agent may be used to form an aqueous gel system, for example cellulose materials. In those devices where the reservoir is a matrix-type reservoir, it may be formed from any polymeric material in which sufentanil has some solubility within a desired solubility range, for example, a polyurethane, ethylene/vinyl acetate copolymer (EVA), polyacrylate, styrenic block copolymer, and the like. It is preferred that the reservoir 6 is an adhesive type matrix, formed from a pharmaceutically acceptable pressure sensitive adhesive, preferably a polyisobutylene, polyacrylate or a styrenic block copolymer-based adhesive.

More particularly, in those embodiments of the invention where the transdermal delivery system is provided as a monolithic, adhesive matrix device, the reservoir 6 can be formed from standard pressure sensitive adhesives known in the art. Suitable pressure sensitive adhesives for use in the practice of the invention thus include, but are not limited to, polyacrylates, polysiloxanes, polyisobutylene (PIB), polyisoprene, polybutadiene, styrenic block polymers, blends and combinations of the above, and the like. Suitable styrenic block copolymer-based adhesives include, but are not limited to, styrene-isoprene-styrene block copolymer (SIS), styrene-butadiene-styrene copolymer (SBS), styrene-ethylenebutene-styrene copolymers (SEBS), and di-block analogs thereof. Suitable acrylic polymers are comprised of a copolymer or terpolymer comprising at least two or more exemplary components selected from acrylic acids, alkyl acrylates, methacrylates, copolymerizable secondary monomers or monomers with functional groups. Examples of monomers include, but are not limited to, acrylic acid, methacrylic acid, methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate, methoxyethyl methacrylate, and the like. See, e.g., Satas (1989) "Acrylic Adhesives," *Handbook of Pressure-Sensitive Adhesive Technology*, 2nd ed., pp. 396-456 (D. Satas, ed.), Van Nostrand Reinhold, N.Y. In a preferred embodiment, the pressure-sensitive adhesive is an acrylate having no functional groups or cross linkers (e.g., DURO-TAK® 87-9301, available from National Starch & Chemical, Bridgewater, N.J.), or a blend of acrylate-vinylacetates having —COOH and —OH functional groups (DURO-TAK® 87-2051 and 87-2287, National Starch & Chemical).

In certain other preferred embodiments, the reservoir 6 is formed from a monolithic adhesive matrix containing a polyisobutylene material. The polyisobutylene preferably comprises a blend of a high molecular weight polyisobutylene (about 450,000 to 2,100,000 viscosity average molecular weight) and a low molecular weight polyisobutylene (about 1,000 to 450,000 viscosity average molecular weight). In the polyisobutylene compositions of the present invention it is preferred that the high molecular weight:low molecular weight polyisobutylene in these compositions are used in a ratio of from about 20:80 to about 70:30, preferably between about 40:60 to about 50:50.

In a particularly preferred embodiment, the pressure-sensitive adhesive is a combination of low and high molecular weight polyisobutylene (PIB) polymers, for example, a high molecular weight PIB having a viscosity average molecular weight of about 1,100,000 (OPANOL® B100, available from BASF, North Mount Olive, N.J.) and a low molecular weight PEB having a viscosity average molecular weight of about 50,000-55,000 (OPPANOL® B 12, available from BASF). In another preferred embodiment, the pressure-sensitive adhesive is a combination of a high molecular weight PIB having a viscosity average molecular weight of about 1,100,000 (VISTANEX® MM L-100, available from ExxonMobil, Houston, Tex.) and a low molecular weight PIB having a viscosity average molecular weight of about 50,000-55,000 (OPPANOL® B 11 SFN, available from BASF).

In practice, the material forming the reservoir 6 has a solubility for the drug of about 1 wt % to about 25 wt % of the total reservoir material; preferably about 2 wt % to about 20 wt %; more preferably about 4 wt % to about 15 wt %; and even more preferably about 6 wt % to about 12 wt %. The reservoir 3, with or without the adhesive coating 6, has a thickness of about The reservoir 6 further includes the sufentanil agent and may also contain other optional ingredients, such as carriers, vehicles, additives, excipients, stabilizers, dyes, diluents, plasticizers, tackifying agents, crystallization inhibitors, solubility enhancers, inert fillers, antioxidants, anti-irritants, vasoconstrictors and other materials without pharmacological activity that are suitable for administration in conjunction with the transdermal delivery systems of the present invention. These optional materials are pharmaceutically acceptable in that they are nontoxic, do not interfere with delivery of sufentanil from the system, and are not for any other reasons biologically or otherwise undesirable. If a pressure sensitive adhesive is used in accordance with the present invention, this must also be pharmaceutically acceptable. Examples of illustrative materials include water, mineral oil, silicone, inorganic gels, aqueous emulsions, liquid sugars, waxes, petroleum jelly, and a variety of other oils and polymeric materials.

Accordingly, in certain transdermal delivery systems of the invention where the reservoir is an adhesive matrix, the reservoir 6 comprises one or more materials capable of improving its adhesive characteristics such as by reducing quick tack (tackifying agents), reducing cold-flow, increasing viscosity, and/or toughening the matrix structure. Examples of suitable materials include, but are not limited to, aliphatic hydrocarbons; aromatic hydrocarbons; hydrogenated esters, polyterpenes, polybutenes, silicone dioxide, silica, hydrogenated wood resins; tackifying resins, aliphatic hydrocarbon resins made from cationic polymerization of petrochemical feedstocks or the thermal polymerization and subsequent hydrogenation of petrochemical feedstocks, rosin ester tackifiers, mineral oil, polybutylmethacrylate, high molecular weight acrylates, and any combinations thereof.

In certain systems, the reservoir 6 comprises one or more viscosity-enhancing agents that improve the adhesive properties of the device, for example by allowing for removal and replacement. The viscosity-enhancing agent may further serve to reduce the abuse potential of the transdermal delivery system by preferentially associating with the sufentanil agent to provide a highly viscous composition that resists extraction of the sufentanil agent under typical abuse conditions (alcohol extraction). The material can be a high viscosity liquid carrier material ("HVLCM") that is non-water soluble, and has a viscosity of at least 5,000 cP, (and optionally at least 10,000, 15,000; 20,000; 25,000 or even 50,000 cP) at 37° C. and that does not crystallize neat under ambient or physiological conditions. The term "non-water soluble" refers to a material that is soluble in water to a degree of less than one percent by weight under ambient conditions. A particularly preferred viscosity-enhancing agent is sucrose acetate isobutyrate (SAIB) or some other ester of a sugar alcohol moiety with one or more alkanoic acid moieties. These materials have bioadhesive qualities.

In practice, a small amount of the SAIB or similar viscosity-enhancing agent is added to a pressure-sensitive material such as a PIB or acrylic adhesive base. Due to the low hydrophobicity and low surface tension of the SAIB material, this enables the resultant adhesive/viscosity agent mixture to retain pressure sensitive properties even after the system has been applied and removed from the skin surface a number of times. This in turn allows the subject wearing a long-duration patch to remove the device during showering or heavy exercise, and then reapply the device without losing adhesion.

In those systems where a plasticizer is utilized, the reservoir can further comprise a plasticizer material that is typically an inert, organic, apolar, nonvolatile hydrophobic liquid. In particular, the plasticizer may be a hydrophobic liquid. Suitable plasticizer materials thus include, but are not limited to, various long-chain aliphatic esters and alcohols, including such materials as polybutene, mineral oil, linseed oil, octyl palmitate, squalene, squalane, silicone oil, isobutyl stearate, olive oil, isopropyl myristate, isostearyl alcohol, oleyl alcohol, and the like. Particularly preferred for use herein is polybutene, for example IDOPOL® L-14 or H-100, available from BP Amoco, Naperville, Ill.), having a viscosity substantially equivalent to light mineral oil.

In addition, the reservoir can include one or more filler materials. Suitable fillers include, but are not limited to, metal oxides, inorganic salts, synthetic polymers, clays and the like. The metal oxides may be silicon dioxide, zinc oxide, magnesium oxide, titanium oxide, and calcium oxide. Inorganic salts can be calcium, magnesium and sodium carbonate, calcium and magnesium sulfate, calcium phosphate, and the like. Synthetic polymers can include methacrylic resin, nylon, polyethylene, and the like. Suitable clay compounds include talc, bentonite and kaolin.

Referring again to FIGS. 1 and 2, the device 2 further comprises a peelable release liner 8. The release liner is a disposable element that serves only to protect the device prior to application to the skin. Typically, the release liner is formed from a material impermeable to the sufentanil agent and other components of the system, and is easily removable from the reservoir. Release liners can generally be made of the same materials as the backing layer. Suitable materials thus include a polymeric material that may be optionally metallized. Examples of the polymeric materials include polyurethane, polyvinyl acetate, polyvinylidene chloride, polypropylene, polycarbonate, polystyrene, polyethylene, polyethylene terephthalate, polybutylene terephthalate, paper, and the like, and a combination thereof. In preferred embodiments, the protective layer comprises a siliconized polyester sheet, or has a fluoropolymer coating. Particularly preferred materials are SCOTCHPAK® 9744 (available from 3M), and MEDIRELEASE® 2249 (available from Mylan Tech., St. Paul, Minn.).

Referring now to FIG. 2, certain transdermal delivery systems of the invention may include an adhesive layer 10 that serves to adhere the device 2 to the skin. The adhesive layer 10 is generally a drug-permeable pressure sensitive adhesive that is applied over the reservoir. Standard pressure sensitive adhesives are well known in the art. Suitable pressure sensitive adhesives for use in the adhesive layer 10 thus include, but are not limited to, polyacrylates, polysiloxanes, polyisobutylene (PIB), polyisoprene, polybutadiene, styrenic block polymers, blends and combinations of the above, and the like. These materials are disclosed in greater detail hereinabove. The adhesive layer may also serve the purpose of a rate controlling layer or membrane. However, in some systems, a further layer 12 is added as a rate controlling membrane. Suitable rate controlling membrane materials are known in the art and include, but are not limited to, low to high density polyethylene, ethylene vinyl acetate, polyurethane, and styrene poly-butadiene.

The sufentanil agent is incorporated into the transdermal delivery systems of the present invention in a free base form. In particular, the chemical name for sufentanil is: N-[4-(methoxymethyl)-1-[2-(2-thienyl)ethyl]-4-piperidinyl]-N-phenylpropanamide. The molecular weight of sufentanil base is 386.56, and it has the following structural formula:

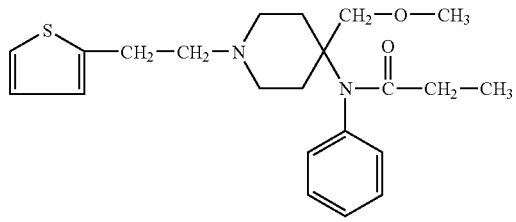

The sufentanil agent is added to the reservoir in an amount of from about 0.1 mg/cm$^2$ to about 2 mg/cm$^2$, preferably in an amount of from about 0.3 mg/cm$^2$ to about 0.8 mg/cm$^2$, and even more preferably in an amount of about 0.4 mg/cm$^2$ to about 0.7 mg/cm$^2$.

Although a number of different transdermal delivery system configurations are suitable for use in practicing the current invention, it is preferred that the systems are provided as a monolithic device, where the sufentanil is contained in an adhesive matrix adhered to a backing layer. Accordingly, in one embodiment of the invention, a monolithic transdermal delivery system for administering sufentanil through the skin is provided. The system includes a pressure-sensitive adhesive matrix that contains sufentanil in an amount above the solubility of sufentanil in the matrix. When the system is applied to a subject, the system provides a substantially constant steady state net flux of sufentanil from the system through the skin of at least about 1 μg/cm$^2$/hour for at least about 24 hours. The system does not include a permeation enhancer or rate controlling membrane. Here again, it is surprising that such high net flux systems that do not employ a permeation enhancer or rate controlling membrane can still perform to such high standards, where upon achieving steady state conditions, the system provides at least a first order release rate profile such that the system achieves substantially zero order release to provide a constant steady state flux of sufentanil from the system over an extended period of time. In certain systems, the system provides a substantially constant steady state net flux of sufentanil from the system through the skin of at least about 1 μg/cm$^2$/hour for at least about 36 hours Additionally, certain systems are also able to provide an even higher steady state net flux net flux of sufentanil from the system through the skin, for example at least about 1.5 μg/cm$^2$/hours in some system, or even around 2 μg/cm$^2$/hour in other systems. In certain preferred systems, the overall size of the transdermal delivery system is kept to minimum, such that the adhesive matrix has a drug releasing interface surface area of from about 1-10 cm$^2$.

In certain of the instant constant steady state flux transdermal delivery systems of the present invention, the sufentanil agent can be present in an amount of about 1-20 weight percent (wt %) relative to the total system, preferably in an amount of about 1-12 wt %. The transdermal delivery systems are provided with sufficient amount of the sufentanil agent to provide for a steady state net flux sufficient to administer the sufentanil at from about 0.01 to 200 μg/hour when the system is applied to the skin of a subject. Still other systems of the present invention provide a steady state net flux sufficient to administer sufentanil at from about 1 to 20 μg/hour when the system is applied to the skin of a subject, while further systems are able to provide a steady state net flux sufficient to administer sufentanil at from about 1 to 2 μg/hour. The present systems contain a sufficient amount of sufentanil so that they may be used to induce and maintain a suitable state of analgesia in a subject for 3 or more days when applied to the skin of that subject. Other systems contain a sufficient amount of sufentanil to induce and maintain a suitable state of analgesia in a subject for 5 or more days, while still others contain enough to induce and maintain a suitable state of analgesia in a subject for 7 or more days.

In another related embodiment of the invention, a monolithic transdermal delivery system for administering sufentanil through the skin is provided. The system includes a pressure-sensitive adhesive matrix that contains sufentanil in an amount above the solubility of sufentanil in the matrix. When the system is applied to a subject, the system provides a net flux of sufentanil from the system through the skin of at least about 1 μg/cm$^2$/hour. The system provides a dosage form rate control over flux of sufentanil from the system, but the system does not include a permeation enhancer or rate controlling membrane. In these systems, the sufentanil is provided as a depot, and is thus present in the system in an amount above the solubility of sufentanil in the system, such that there will be both dissolved and undissolved sufentanil in the system. In certain systems, the dosage form rate control $$\left( \frac{J_N}{J_D} \right)$$

over flux of sufentanil from the system is at least about 50% while still providing the substantially high rate of net flux from the system. In certain systems, the dosage form rate control $$\left(\frac{J_N}{J_D}\right)$$

over flux of sufentanil from the system is even higher, for example at least about 60%, while in still other systems the dosage form rate control is at least about 65%. As with the other systems of the present invention, the dosage form rate control can be provided by a number of different mechanisms/components, either alone or in combination. Thus, the dosage form rate control can be provided at least in part by using a pharmaceutically acceptable adhesive matrix carrier composition and/or a rate controlling membrane. Despite not including a permeation enhancer or rate controlling membrane, certain systems are able to provide an even higher net flux of sufentanil from the system through the skin, on the order of at least about 1.5 µg/cm²/hour, while still others can provide a net flux of around 2 µg/cm²/hour.

In certain of the subject monolithic systems, the sufentanil agent can be present in an amount of about 1-20 weight percent (wt %) relative to the total system, preferably in an amount of about 1-12 wt %. The instant transdermal delivery systems are provided with sufficient amount of the sufentanil agent to provide for a steady state net flux sufficient to administer the sufentanil at from about 0.01 to 200 µg/hour when the system is applied to the skin of a subject. Certain other systems of the present invention provide a steady state net flux sufficient to administer sufentanil at from about 1 to 20 µg/hour when the system is applied to the skin of a subject, while still further systems are able to provide a steady state net flux sufficient to administer sufentanil at from about 1 to 2 µg/hour. It is a surprising feature of the instant systems in that they can also provide a substantially constant steady state net flux of sufentanil from the system through the skin for at least about 24 hours. Certain other systems are further able to provide a substantially constant steady state net flux ($J_N$) of sufentanil of at least about 1.5 µg/cm²/hour. Still others are able to provide a substantially constant steady state net flux ($J_N$) of sufentanil for at least about 36 hours. In certain preferred systems, the overall size of the transdermal delivery system is kept to minimum, such that the adhesive matrix has a drug releasing interface surface area of from about 1-10 cm².

The monolithic transdermal delivery systems contain a sufficient amount of sufentanil so that they may be used to induce and maintain a suitable state of analgesia in a subject for 3 or more days when applied to the skin of that subject. Other systems contain a sufficient amount of sufentanil to induce and maintain a suitable state of analgesia in a subject for 5 or more days, while still others contain enough to induce and maintain a suitable state of analgesia in a subject for 7 or more days.

In yet a further related embodiment of the invention, a transdermal delivery system for administering sufentanil through the skin of a living subject is provided. The subject system provides a substantially constant delivery rate of sufentanil over a single application administration period of at least about 48 hours and the constant delivery rate is sufficient to establish and maintain a plasma sufentanil concentration having a maximum to minimum ratio of about 1.8 or less over the relevant administration period. In certain systems, the delivery rate of sufentanil from the transdermal delivery system is substantially zero order. In others, the delivery rate of sufentanil is characterized by a total decline or increase of about 5 to 6% over the administration period, and preferably, the delivery rate of sufentanil is characterized by substantially no total increase or decrease over the administration period. The subject transdermal delivery systems are able to provide a delivery rate at steady state of at least about 1 µg/hr to 10 µg/hr, and the administration period extends from at least about 48 hours to 7 days. Additionally, all of the above-described transdermal delivery systems of the present invention can be engineered to provide a substantially constant delivery rate of sufentanil over a single application administration period of at least about 48 hours, wherein the constant delivery rate is sufficient to establish and maintain a plasma sufentanil concentration having a maximum to minimum ratio of about 1.8 or less over the relevant administration period.

All of the transdermal delivery systems of the present invention can be readily manufactured using known techniques. For example, to produce matrix-type systems, a solution of a suitable polymeric reservoir material can be added to a double planetary mixer, followed by addition of desired amounts of the sufentanil base. Typically, the polymeric reservoir material is an adhesive polymer, which can be solubilized in an organic solvent, e.g., ethanol, ethyl acetate, and hexane. After mixing has taken place for a suitable period of time to achieve acceptable uniformity of the ingredients, the resultant mixture can be feed into a casting die. In such cases, the matrix/sufentanil mixture is cast as a wet film onto a moving web or belt, which is drawn through lines and a series of ovens are then used to evaporate the casting solvent to acceptable residual limits. The dried reservoir film can then be laminated to a selected backing membrane that is wound onto take-up rolls. In subsequent operations, individual transdermal patches are die-cut, separated and unit-packaged. In other processes, a reservoir can be formed using dry-blending and thermal film-forming using equipment known in the art. Preferably, the materials are dry blended and extruded using a slot die followed by calendering to an appropriate thickness.

When manufacturing certain preferred monolithic systems according to the invention that include a polyisobutylene/polyisobutylene blend as the matrix, it is preferable to use a solvent for the polyisobutylene that is a non-solvent for the sufentanil, such as low molecular weight hydrocarbon solvents like heptane, hexane, or cyclohexane. Preferably, the mixture of polyisobutylene compositions includes from about 65 to 90% by weight of the solvent, more preferably from about 70 to about 85% by weight of the solvent.

A preferred manufacturing process for a monolithic transdermal delivery system prepared according to the invention is as follows. Pre-weighed amounts of both high and low molecular weight PIB and polybutene are added into glass vessels containing pre-measured amount of n-heptane and the containers are sealed. The PIB fractions and polybutene in the sealed containers are completely dissolved in n-heptane at room temperature using magnetic stirring equipment. Mixing of the n-heptane polymer solution may continue in case when one or more of the inactive ingredients needs to be added in the polybutene-PIB formulations. Typical mass ratios of the low molecular weight PIB, high molecular weight PIB, polybutene oil and n-heptane are: 1.23:1:2.1:10.1, respectively. Selective additives in small quantities can be added at the expense of all other non-solvent materials in the solution.

A pre-weighed amount of sufentanil is added to the above n-heptane solutions of polybutene-polyisobutylene and the sufentanil suspension is homogeneously mixed for approximately 2 days for complete equilibration of sufentanil and the vehicle, using magnetic stirring equipment at room temperature. Then, stirring action is stopped for approximately 15 minutes, air bubbles are removed from the sufentanil suspension, which is now ready to be transferred on a piece of release liner for precision-thickness coating of the suspension using either a motorized film applicator (Elcometer, Inc.) or precision glass plates and square multiple clearance applicators (Gardner PG&T Co.).

The wet suspension films on release liner section are air-dried for approximately 20 minutes at room temperature and 30 minutes at 70° C. in a convection oven (Blue M Electric, CSP Series Class A Oven). The oven dried sufentanil suspension films coated on the release liner film (reservoir/release liner laminate) are cooled to room temperature and a precut piece of the backing film is laminated onto the reservoir/release liner laminate, which is still sitting on a precision glass plates. A aluminum roller (diameter: 1 in., length: 4 in.) or a piece of lamination equipment (Roll over Roll Coater, SciMac Scientific Machine) is used to aid the lamination step by squeezing and eliminating air pockets out of the reservoir/release liner laminates.

The final steps of the sufentanil transdermal delivery system fabrication include die cutting the final laminates, using steel rule dies and a punch press (Schmidt Toggle Press, Schmidt Feintechnik Corp.) into required system size (Apex Die, Inc.). Appearance of the cut edges of the systems is examined. The total thickness and weight of the systems are determined using a pair of calipers (Mitutoyo Corp.) and a precision balance, respectively and recorded.

The systems are then placed into aluminum foil pouches, and the open ends of the pouches are heat sealed using an impulse heat sealer (Impulse Heat Sealer, Clamco). The pouches are labeled appropriately and counted and recorded.

Figure 3:
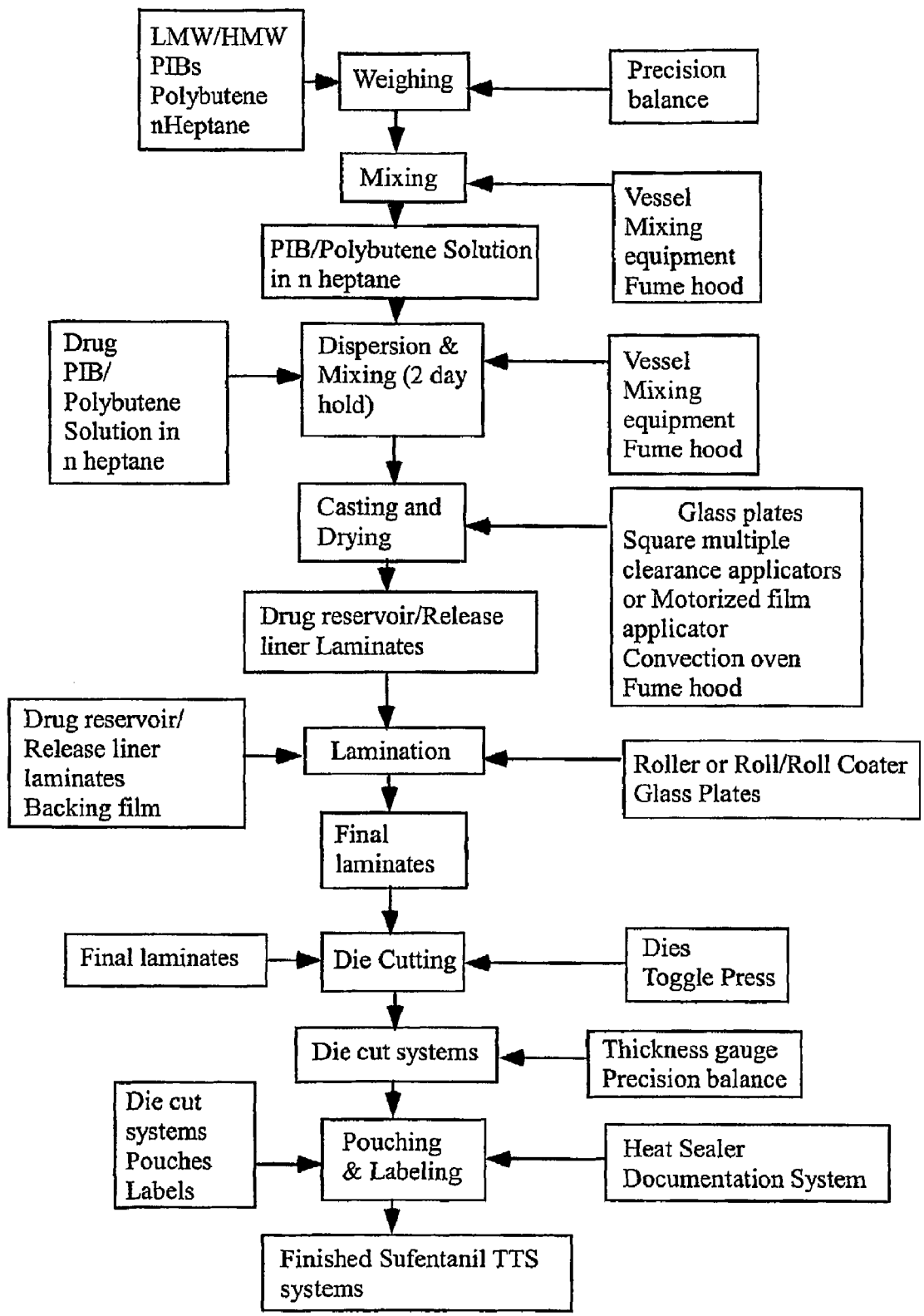
FIG. 3 present a schematic representation of a manufacturing process for producing a transdermal delivery system according to the present invention.
Figure 4:
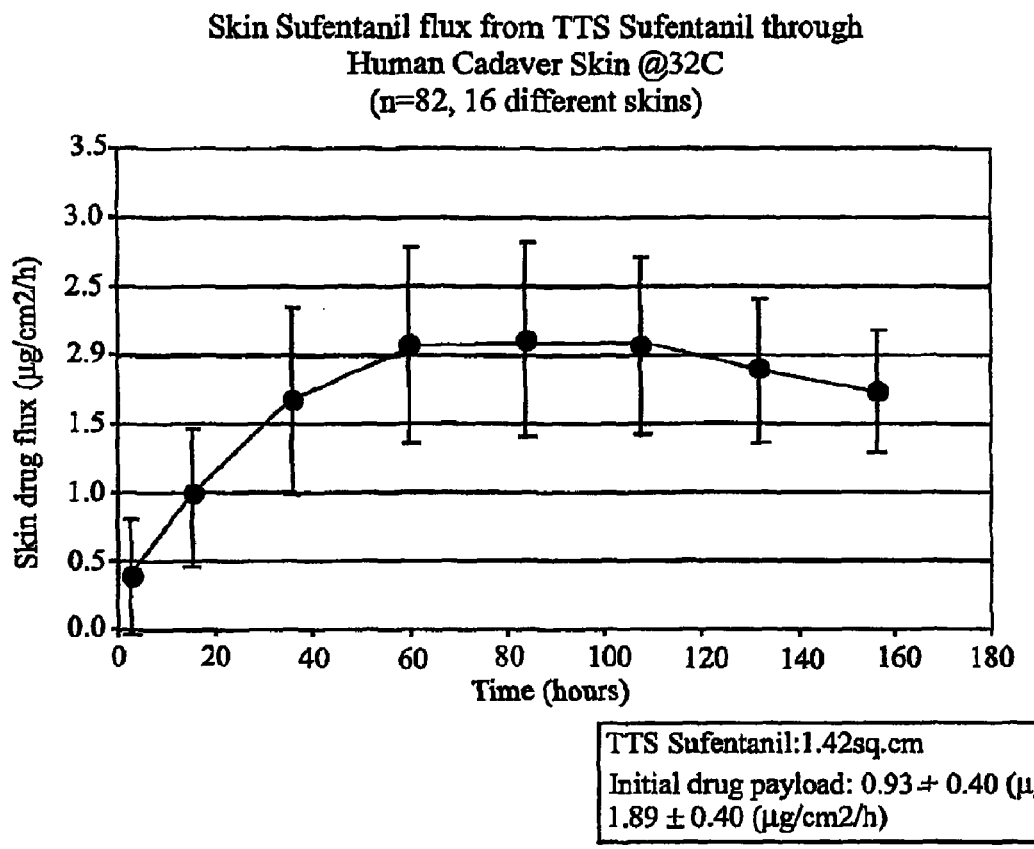
FIG. 4 depicts the results from the Example 1 in vitro skin flux study using a transdermal delivery system according to the present invention.

Referring now to FIG. 3, a flow diagram illustrating the system manufacturing steps, along with materials, tools and equipment that are required for each unit operation for the systems is provided.

Once the transdermal delivery systems are produced, they are used to provide an extended period of analgesia in a subject using the following methods. The term "subject," as used herein, is used interchangeably with "individual" and refers to any vertebrate in which it is desired to provide a state of analgesia. The term thus broadly refers to any animal that is to be treated with the systems of the present invention, such as birds, fish and mammals including humans. In certain embodiments, the systems and methods of the present invention are suitable to provide sustained analgesia in veterinary practice and animal husbandry, e.g., birds and mammals, whenever a long-term state of analgesia is convenient or desirable. In certain cases, the compositions are particularly suited for used with companion animals such as dogs or cats, and additionally may be used with horses. In preferred embodiments, the term "subject" intends a human subject. Furthermore, the term "subject" does not denote a particular age, and the present systems are thus suited for use with subjects of any age, such as infant, adolescent, adult and senior aged subjects.

A suitable transdermal delivery system containing sufentanil and prepared according to the present invention is applied to a clean, dry and preferably non-hairy area of skin on a subject, for example, the inner upper arm surface or upper buttock. It is intended that different skin sites are chosen for subsequent system applications. Upon application to the skin, the sufentanil in the reservoir of the transdermal delivery system will diffuse into the skin where it is absorbed into the bloodstream to produce a systemic analgesic effect.

The onset of analgesia depends on various factors, such as, potency of the sufentanil, the solubility and diffusivity of sufentanil in the skin, the thickness of the target skin, the concentration of sufentanil in the device reservoir, and the like. Generally, the subject will experience an adequate effect within about one to six hours of initial application. When continuous analgesia is desired, a depleted system is removed and a fresh system applied to a new location. For example, the 3 to 7 day systems of the present invention can be sequentially removed and replaced with a fresh system at the end of the administration period to provide relief from chronic pain. Substantially uninterrupted sequential system applications can thus be used to maintain plasma sufentanil levels at a substantially constant level. Additionally, it is contemplated that doses may be increased over time, and that concurrent use of other analgesics may occur to deal with breakthrough pain.

EXAMPLES

Below are examples of specific embodiments for carrying out the present invention. The examples are offered for illustrative purposes only, and are not intended to limit the scope of the present invention in any way.

Example 1

In Vitro Sufentanil Flux Through Human Skin

In-vitro permeation sufentanil flux studies were conducted with human skin from cadaver donors (dermatomed full thickness). Thigh skin from sixteen different donors was used in the experiments, with a minimum of 5 replicate skin samples per donor (total n=82). Prior to the in vitro skin drug flux experiment, the skin tissue was examined under a magnifying glass for any defects such as pinholes. Excluding any damaged areas, the intact skin areas were cut into 1-inch circles. Monolithic adhesive matrix patches using a high molecular weight/low molecular weight polyisobutylene (PIB) blend for the adhesive was prepared as described above. In the tests, a sufentanil transdermal delivery system was placed on the stratum corneum side of the pre-cut skin sample. Then, the assembly of system and pre-cut skin specimen was positioned on the top edge of the receptor side of a modified Franz cell with the dermal side of the skin tissue facing the receptor chamber. The donor side of the Franz Cell was securely positioned over the skin/system assembly, and the receptor chamber was filled with citrate buffer at pH 5.0 containing 0.01% sodium azide. The Franz cell with the test system was equilibrated at 32° C. for the duration of the experiment. At predetermined intervals (typically 6 hours, 1, 2, 3, 4, 5, 6 and 7 days), the entire receptor solution was collected from the Franz cell and refilled with fresh receptor medium. The receptor solutions were assayed for sufentanil concentration using a HPLC chromatographic method. The cumulative delivery amount and skin drug flux were calculated for each skin/test system assembly. FIG. 3 illustrates the actual sufentanil skin flux over 7 days through human cadaver specimens from the 16 different donors. The overall average sufentanil skin flux was approximately 1.9 µg/cm$^2$/hr, with a coefficient of variation of 40%.

Example 2

In Vitro Sufentanil Flux from Transdermal Delivery System

A sufentanil transdermal delivery system having a drug releasing interface surface area of 1 cm$^2$ or 1.42 cm$^2$ Monolithic adhesive matrix patches, using a high molecular weight/low molecular weight polyisobutylene (PIB) blend for the adhesive and containing sufentanil were prepared as described above.

In the test, the sufentanil transdermal delivery system was held adhesively on a stainless steel holder, having the drug releasing surface of the patch facing up and immersable in release medium, and positioned at the center of a USP Dissolution Apparatus II with 1 L vessels. Accurately, 600 mL of degassed 0.005N sodium phosphate, pH 5.5 buffer solution was placed in the vessels and maintained at 32° C. while the paddle speed was maintained at 50 rpm during the dissolution experiment.

At the preset time intervals of 1, 2, 4, 8, 12, 16, 24, 36, and 48 hours, 1 mL portions of the dissolution medium was withdrawn from the vessels and dispensed into HPLC vials. The following conditions were used for the sufentanil assay in the samples:

| | |
|---|---|
| Mode: | Isocratic |
| Mobile Phase: | A - 75% 0.1% triethylamine in $H_2O$ (adjusted to pH = 3.0 with $H_3PO_4$) |
| | B - 25% 100% acetonitrile |
| Stop Time: | 4.0 minutes |
| Post time: | None |
| Column Temperature: | 40° C. |
| Flow Rate: | 1.0 mL/min |
| UV Detection: | 230 nm |
| Injection Volume: | 10 µL |
| Autosampler Temperature: | ambient room temperature |
| Retention time: | 2 minutes |

From the sufentanil concentration, total volume of the buffer solution remaining in the vessels and time intervals, it was possible to calculate the cumulative amounts of sufentanil dissolved or released from the patches over time, and dissolution rate or release rate of sufentanil from the sample transdermal delivery systems were calculated.

Figure 5A:
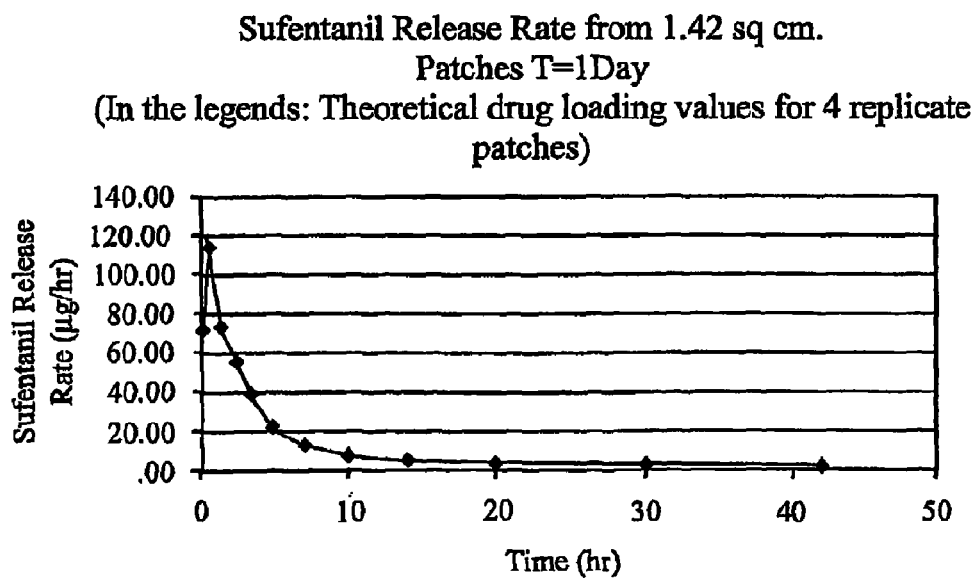
FIGS. 5A and 5B depict the results from the Example 2 in vitro system flux study using a transdermal delivery system according to the present invention.
Figure 5B:
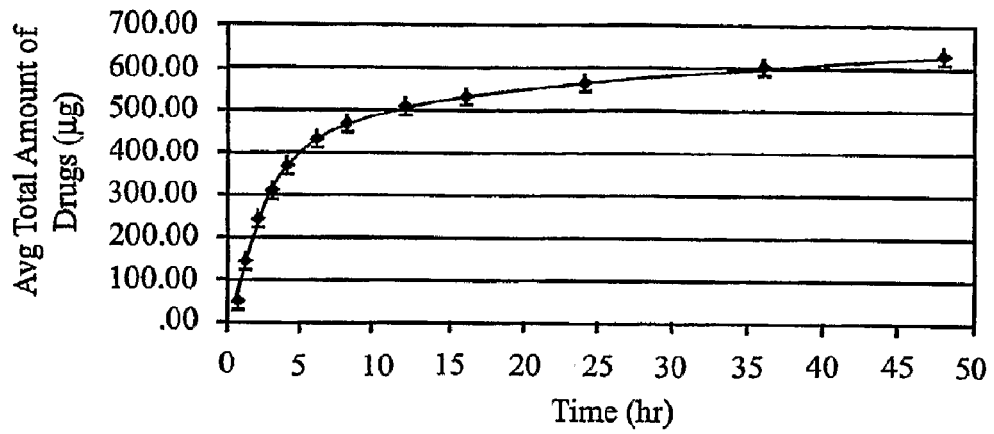

The results from the dissolution rate test are presented in FIGS. 5A and 5B, and provided below in Tables 1 and 2.

TABLE 1

| Sampling Time (hours) | Total Amount of Sufentanil (µg) Vessel 1 | Total Amount of Sufentanil (µg) Vessel 2 | Total Amount of Sufentanil (µg) Vessel 3 | Total Amount of Sufentanil (µg) Vessel 4 | Average | SD | Average % Initial Sufentanil Loading Released |
|---|---|---|---|---|---|---|---|
| 0.5 | 59.5 | 59.81 | 58.10 | 49.66 | 56.71 | 4.75 | 6.56 |
| 1 | 137.48 | 146.58 | 142.16 | 140.91 | 141.78 | 3.76 | 16.39 |
| 2 | 236.93 | 251.04 | 242.34 | 243.48 | 243.45 | 5.81 | 28.14 |
| 3 | 309.37 | 334.27 | 318.36 | 321.13 | 320.78 | 10.30 | 37.08 |
| 4 | 371.07 | 399.54 | 387.28 | 386.72 | 386.15 | 11.67 | 44.64 |
| 6 | 445.24 | 467.06 | 441.88 | 443.05 | 449.31 | 11.92 | 51.94 |
| 8 | 469.14 | 503.65 | 486.94 | 486.77 | 486.62 | 14.09 | 56.26 |
| 12 | 513.76 | 553.54 | 518.40 | 520.91 | 526.66 | 18.17 | 60.88 |
| 16 | 533.20 | 578.49 | 544.58 | 546.57 | 550.71 | 19.44 | 63.67 |
| 24 | 576.36 | 624.70 | 583.73 | 587.56 | 593.09 | 21.58 | 68.57 |
| 36 | 622.85 | 673.35 | 621.61 | 632.56 | 637.59 | 24.34 | 73.71 |
| 48 | 652.20 | 704.98 | 658.56 | 673.27 | 672.25 | 23.53 | 77.72 |

TABLE 2

| Midpoint Time (hour) | Rate (µg/cm²/hr) Vessel 5 | Rate (µg/cm²/hr) Vessel 6 | Rate (µg/cm²/hr) Vessel 7 | Rate (µg/cm²/hr) Vessel 8 | Average | SD |
|---|---|---|---|---|---|---|
| 0.25 | 81.31 | 68.65 | 77.09 | 59.42 | 71.62 | 9.68 |
| 0.5 | 109.95 | 107.80 | 123.80 | 115.59 | 114.28 | 7.14 |
| 1.5 | 73.84 | 70.74 | 74.89 | 70.86 | 72.58 | 2.10 |
| 2.5 | 58.57 | 48.24 | 55.33 | 59.41 | 55.39 | 5.08 |
| 3.5 | 40.21 | 37.21 | 43.66 | 33.42 | 38.62 | 4.35 |
| 5 | 22.76 | 21.60 | 23.56 | 20.22 | 22.03 | 1.45 |
| 7 | 12.68 | 11.32 | 10.90 | 14.25 | 12.29 | 1.51 |
| 10 | 7.75 | 6.50 | 6.12 | 7.96 | 7.08 | 0.91 |
| 14 | 3.23 | 5.68 | 5.26 | 4.65 | 4.70 | 1.07 |
| 20 | 3.20 | 3.18 | 2.31 | 3.38 | 3.02 | 0.48 |
| 30 | 3.09 | 2.01 | 2.10 | 1.96 | 2.29 | 0.53 |
| 42 | 2.08 | 1.64 | 1.44 | 2.34 | 1.88 | 0.41 |

Example 3

Pharmacokinetic Evaluation of Sufentanil Transdermal Delivery System Following a Single Application in Rats Sufentanil transdermal delivery systems having a drug releasing interface surface area of 1 $cm^2$ or 1.42 $cm^2$ (both of which contain approximately 0.67 mg sufentanil free base per $cm^2$) were applied to 5 each of male and female rats of 7 to 8 weeks old (CD (Crl:CD® (SD) 1 GS BR) from Charles River Labs). The systems were monolithic adhesive matrix patches, using a high molecular weight/low molecular weight polyisobutylene (PIB) blend for the adhesive, and were prepared as described above.

At least 16 hours before dosing, the back and shoulders of each animal was shaved and the targeted application areas washed with water. Care was taken not to abrade the skin. One of the transdermal delivery systems was applied to the dorsal midline and held in contact with the skin by elastic wrap placed over the system and around the animal. During the course of the PK study, the animals were given ad libitum certified rodent diet #8728C(Harlan Teklad, Inc) and water, and housed in a controlled environment, temperature of 18-26° C., a relative humidity of 50±20% and a 12 hour light/12 hour dark cycle.

Blood samples (approximately 1 ml each) were collected from each animal at time 0 (before system application) and at 24, 48, 96 and 168 hours after application of the system. Blood was collected via jugular venipuncture and transferred into tubes containing potassium EDTA anticoagulant.

Blood samples were maintained on wet ice, in chilled Kryoracks, or at approximately 5° C. prior to centrifugation to obtain plasma. Centrifugation was carried out within 30 minutes of collection. Plasma samples were transferred to a tube and were maintained on dry ice prior to storage at approximately −70° C.

Sufentanil in the plasma samples was assayed using HPLC. The analytical technique for the determination of sufentanil in rat plasma was as follows. Sufentanil in rat plasma was determined using a HPLC/MS/MS method in the positive electrospray mode. The analytical column was a YMC basic (50×2 mm, 5 u) with mass detection of the transitions 387.4/238.0 amu for sufentanil and 337.4/188.0 amu for the internal standard.

The results of the study are presented below in Table 3.

TABLE 3

| Patch Size, No. of Subjects | Sample Time | Average Plasma Conc. (pg/mL) | Standard Deviation | % RSD |
|---|---|---|---|---|
| 1.0 cm², Male + Female n = 9 | 0 | 0 | 0 | 0 |
|  | 24 | 1232 | 655 | 53 |
|  | 48 | 1428 | 930 | 65 |
|  | 96 | 994 | 331 | 33 |
|  | 168 | 856 | 328 | 38 |
| 1.42 cm², Male + Female n = 10 | 0 | 0 | 0 | 0 |
|  | 24 | 1211 | 412 | 34 |
|  | 48 | 1360 | 493 | 36 |
|  | 96 | 1235 | 384 | 31 |
|  | 168 | 781 | 332 | 43 |

Figure 6:
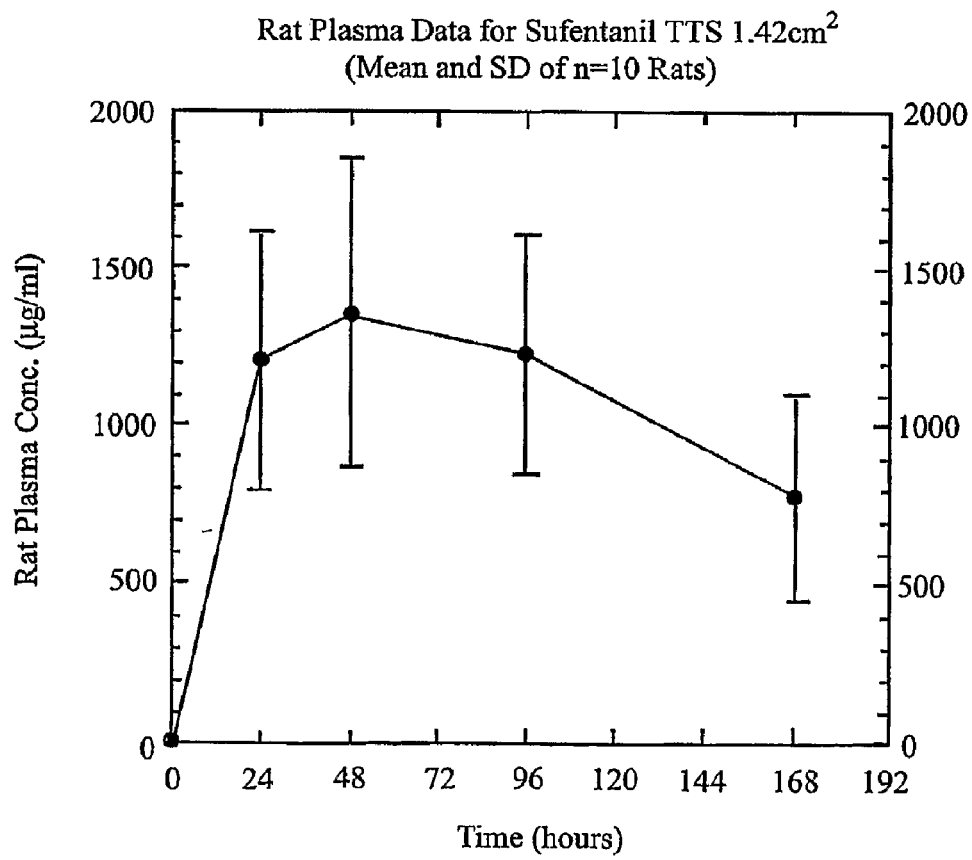
FIG. 6 depicts the results from the Example 3 pharmacokinetic study using a transdermal delivery system having a drug releasing interface surface area of 1.42 cm$^2$.

The data from the 1.42 cm² patch study are also depicted in FIG. 6. As can be seen, the plasma concentration of sufentanil, delivered from a single transdermal delivery system, having a drug releasing interface surface area of 1.42 cm², increased to establish an approximate constant level starting at approximately 24 hours after the system application and continued to maintain the level for 168 hours (7 days). During the course of the 7-day delivery, the plasma concentrations of sufentanil from time 24-168 hours in male and female rats were approximately 1,150±260 pg/ml and 1,140±270 pg/ml, respectively. There is no statistically significant difference in the sufentanil plasma concentrations between the male and female rats, suggesting that both drug delivery rate from the system and pharmacokinetic parameters such as systemic drug clearance do not differ significantly between the two sexes of the rats used in the PK study.

The variability of the sufentanil plasma concentrations is remarkably and equally low in both male and female rats (coefficient of variation of approximately 23%), confirming the fact that not only the variability of systemic clearance of the drug in different rats is low but also most importantly rate controlled drug delivery through the skin of different rats of both sexes from the sufentanil transdermal delivery system is significantly high so as to reduce or virtually eliminate variability in skin sufentanil permeability between rats of both sexes.

Example 3

Preparation of Sufentanil Transdermal Delivery Systems

A series of 3-day and 7-day monolithic adhesive matrix patches, using either a high molecular weight/low molecular weight polyisobutylene (PIB) blend, or acrylic polymers for the adhesive are prepared as follows. The systems include from 1 to 4 mg of sufentanil and are prepared to deliver in human subjects, depending on the system size, from about 90 to 360 μg sufentanil per day, from systems having a drug releasing interface surface area of from 2 to 8 cm², respectively. Each system is individually packaged in an aluminum foil pouch carrying an appropriate pharmaceutical label.

The components for the 7-day systems are listed in Table 4 below.

TABLE 4

| Components | Primary material/Vendor | Regulatory Status | Secondary material/Vendor | Regulatory Status | Notes |
|---|---|---|---|---|---|
| Backing Film | Scotchpak 1109 Backing (3M) | DMF # 2610 | Scotchpak 9733 Backing (3M) | DMF # 14291 | 1109 - laminate of polyethylene and aluminum vapor coated polyester. 9733 - laminate of polyester and polyethylene/ethylene vinyl acetate. |
| High Molecular Weight PIB (polyisobutylene) | Oppanol B100 (BASF) | Conforms to 21 CFR 172.615 (chewing gum base). ISO 9001 Certified | Vistanex MM L-100 (ExxonMobil) | Conforms to 21 CFR 172.615 (chewing gum base). | Viscosity average molecular weight is approx. 1,100,000 |
| Low Molecular Weight PIB (polyisobutylene) | Oppanol B 12 SFN (BASF) | Conforms to 21 CFR 172.615 (chewing gum base). ISO 9001 Certified | Oppanol B 11 SFN (BASF) | Conforms to 21 CFR 172.615 (chewing gum base). ISO 9001 Certified | Viscosity average molecular weight is approx. 50,000-55,000 |
| Polybutene | Indopol L-14 (BP Amoco) | DMF # 17390 | Indopol H-100 (BP Amoco) | DMF # 17390 | Indopol L-14 is viscosity-equivalent to light mineral oil, USP |
| Release Liner | Scotchpak 9744 (3M) | DMF # 15781 | Medirelease 2249 (Mylan Tech) | DMF # 14652 | 3M release liner has a fluoropolymer coating and Mylan's release liner has a silicone coating |

TABLE 4-continued

| Components | Primary material/ Vendor | Regulatory Status | Secondary material/ Vendor | Regulatory Status | Notes |
|---|---|---|---|---|---|
| Pouch | Polyester/foil (Technipaq) | Conforms to appropriate CFR sections | Paper/ polyester/foil (Technipaq) | Conforms to appropriate CFR sections | Approximately 2.75 in × 3.25 in |
| Label | Paper Label (Avery) | Not applicable | None | Not applicable | Product and drug names, system size, drug content, and code number |
| Additional Inactive Ingredients | Colloidal Silicone Dioxide (Cabot) | NF compendial | Povidone/ Crospovidone (BASF) | USP/NF compendial | CSD grade is M5P or M5DP. Povidone grade is Kollidon 30 or crospovidone grade is Kollidon CL-M. |

The components for the 3-day systems are listed in Table 5 below.

TABLE 5

| Components | Primary material/ Vendor | Regulatory Status | Secondary material/ Vendor | Regulatory Status | Notes |
|---|---|---|---|---|---|
| Backing Film | Scotchpak 1109 Backing (3M) | DMF # 2610 | Scotchpak 9733 Backing (3M) | DMF # 14291 | 1109 - laminate of polyethylene and aluminum vapor coated polyester. 9733 - laminate of polyester and polyethylene/ethylene vinyl acetate. |
| Acrylate | Duro-Tak 87-9301 (National Starch & Chemical) | DMF # 7477 | Duro-Tak 87-2051, 87-2287 (National Starch & Chemical) | DMF # 7477 DMF # 7477 | 87-9301 has no functional groups and no cross linkers. 87-205 land 87-2287 have COOH and OH functional groups, respectively, and acrylate-vinylacetates. |
| Release Liner | Scotchpak 9744 (3M) | DMF # 15781 | Medirelease 2249 (Mylan Tech) | DMF # 14652 | 3M release liner has a fluoropolymer coating and Mylan's release liner has a silicone coating |
| Pouch | Polyester/foil (Technipaq) | Conforms to appropriate CFR sections | Paper/ polyester/foil (Technipaq) | Conforms to appropriate CFR sections | Approximately 2.75 in × 3.25 in |
| Label | Paper Label (Avery) | Not applicable | None | Not applicable | Product and drug names, system size, drug content, and code number |
| Additional Inactive Ingredients | Colloidal Silicone Dioxide (Cabot) | NF compendial | Povidone/ Crospovidone (BASF) | USP/NF compendial | CSD grade is M5P or M5DP. Povidone grade is Kollidon 30 or crospovidone grade is Kollidon CL-M. |

Example 4

In Vivo Pharmacokinetic Study with 7-Day Sufentanil Transdermal Delivery Systems Two Sufentanil transdermal delivery systems (patches) were produced, in two sizes each with active surface areas of 2 and 8 cm², and used in a clinical pharmacokinetic performance study. The transdermal patches were produced as 7-day systems using the "primary" material components as described in Table 4 above. In particular, the formulation used to produce the transdermal patches was a follows (on a percentage of total dry weight): Oppanol B100 (15.4%); Oppanol B12 SFN (22.0%); Indopol Polybutene L-14 (48.5%); CAB-O-Sil M-5P (6.4%); and sufentanil (7.7%); with the final patches using a Scotchpak #9744 release liner (3M) and a Scotchpak #1109 backing material (3M). The two sizes of patches were identical in all aspects except that the casting thicknesses were different; that is, "thin" patches were produced having a nominal 15 mil (wet) coating thickness of the bulk matrix/drug formulation, and "thick" patches were produced having a nominal 25 mil (wet) coating thickness of the same bulk formulation. The amount of sufentanil present in the patches was proportional to the casting thicknesses, and therefore "thin" patches had a lower sufentanil drug content per square cm compared to the "thick" patches. The average sufentanil content per patch determined at the time of lot release for the thin and thick sufentanil patch lots, 2 cm² and 8 cm² sizes, used in the present study are summarized in Table 6. As can be seen, the thick 2 cm² and 8 cm² patches had at least about 75% higher sufentanil content compared to the corresponding thin 2 cm² and 8 cm² patches.

TABLE 6

Sufentanil TTS Descriptions and Observed Sufentanil Content

| Lot Number | Code Number | Patch Size (cm²) | Formulation Nominal Casting Thickness | Observed Sufentanil (mg) per Patch at T = 0 (n = 10) |
|---|---|---|---|---|
| 24A | 45-01 | 2 | 15 mil, thin | 0.91 |
| 25A | 47-01 | 2 | 25 mil, thick | 1.70 |
| 24B | 45-02 | 8 | 15 mil, thin | 3.84 |
| 25B | 47-02 | 8 | 25 mil, thick | 6.71 |

Figure 7:
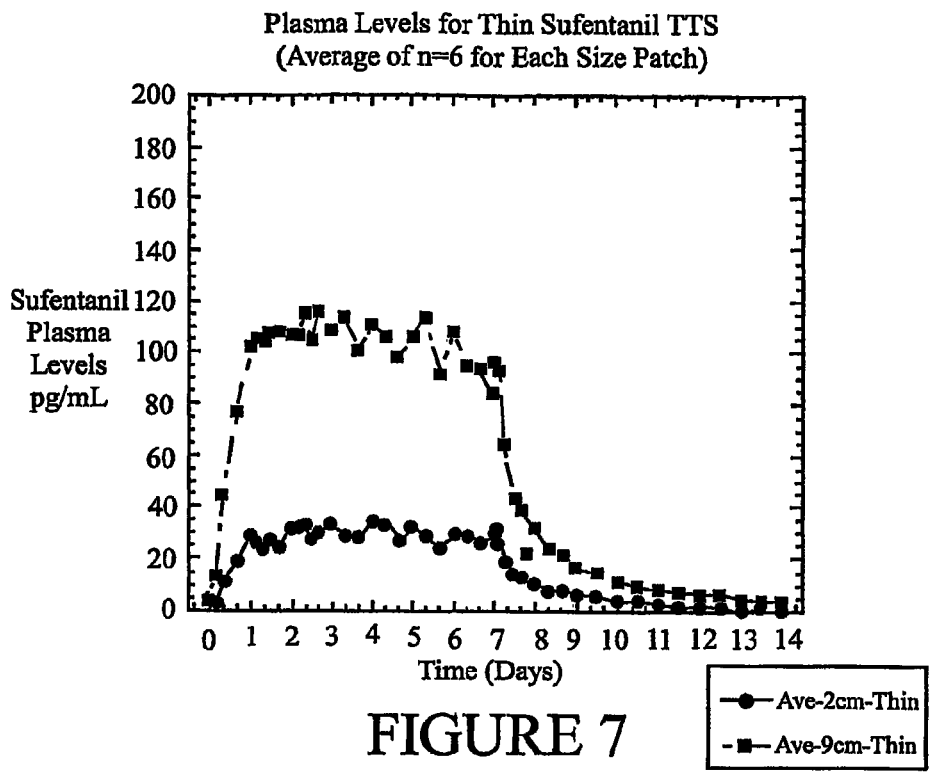
FIG. 7 depicts the measured sufentanil plasma levels from Example 4 for the test subjects wearing "thin" transdermal delivery systems.
Figure 8:
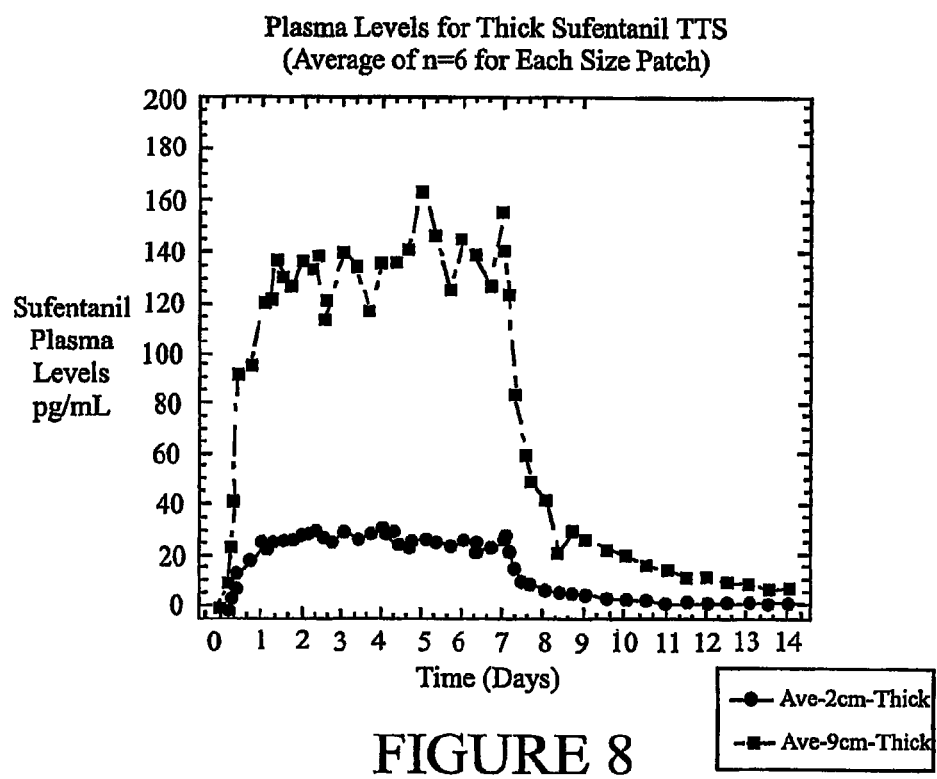
FIG. 8 depicts the measured sufentanil plasma levels from Example 4 for the test subjects wearing "thick" transdermal delivery systems.
Figure 9:
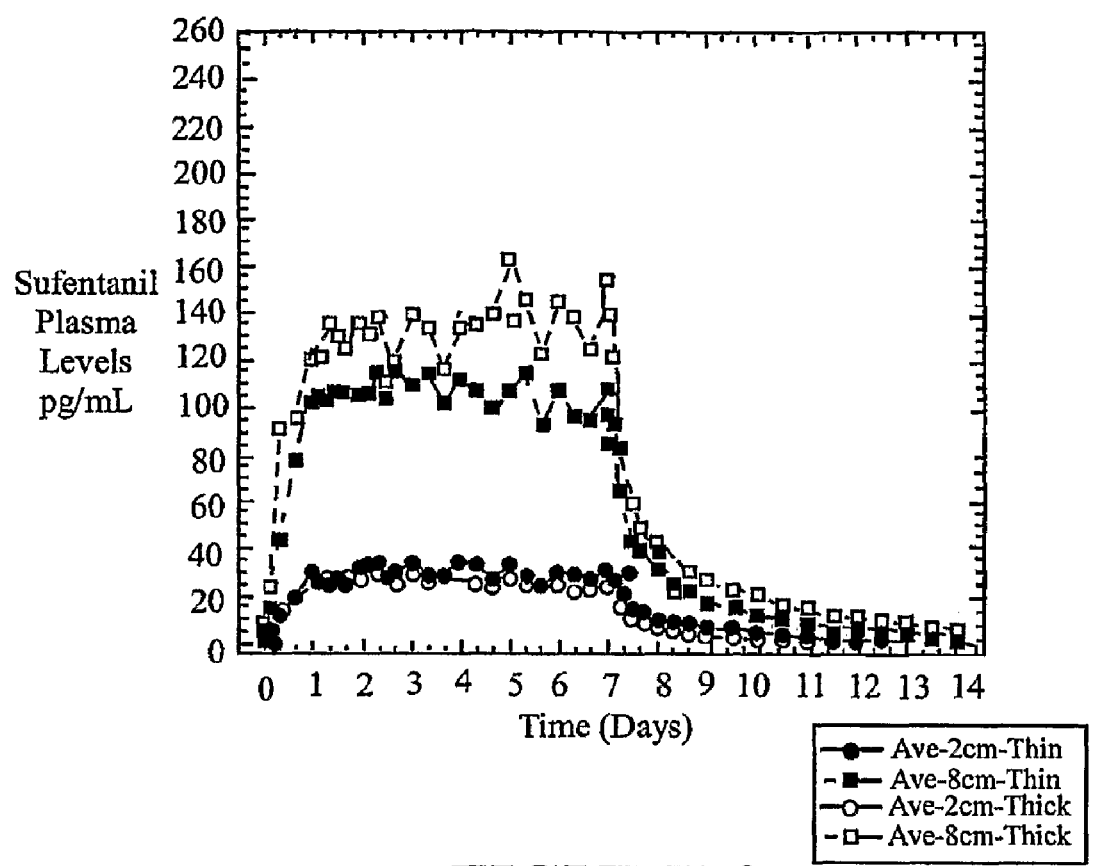
FIG. 9 depicts the average sufentanil plasma levels for all four test groups from Example 4.
Figure 10:
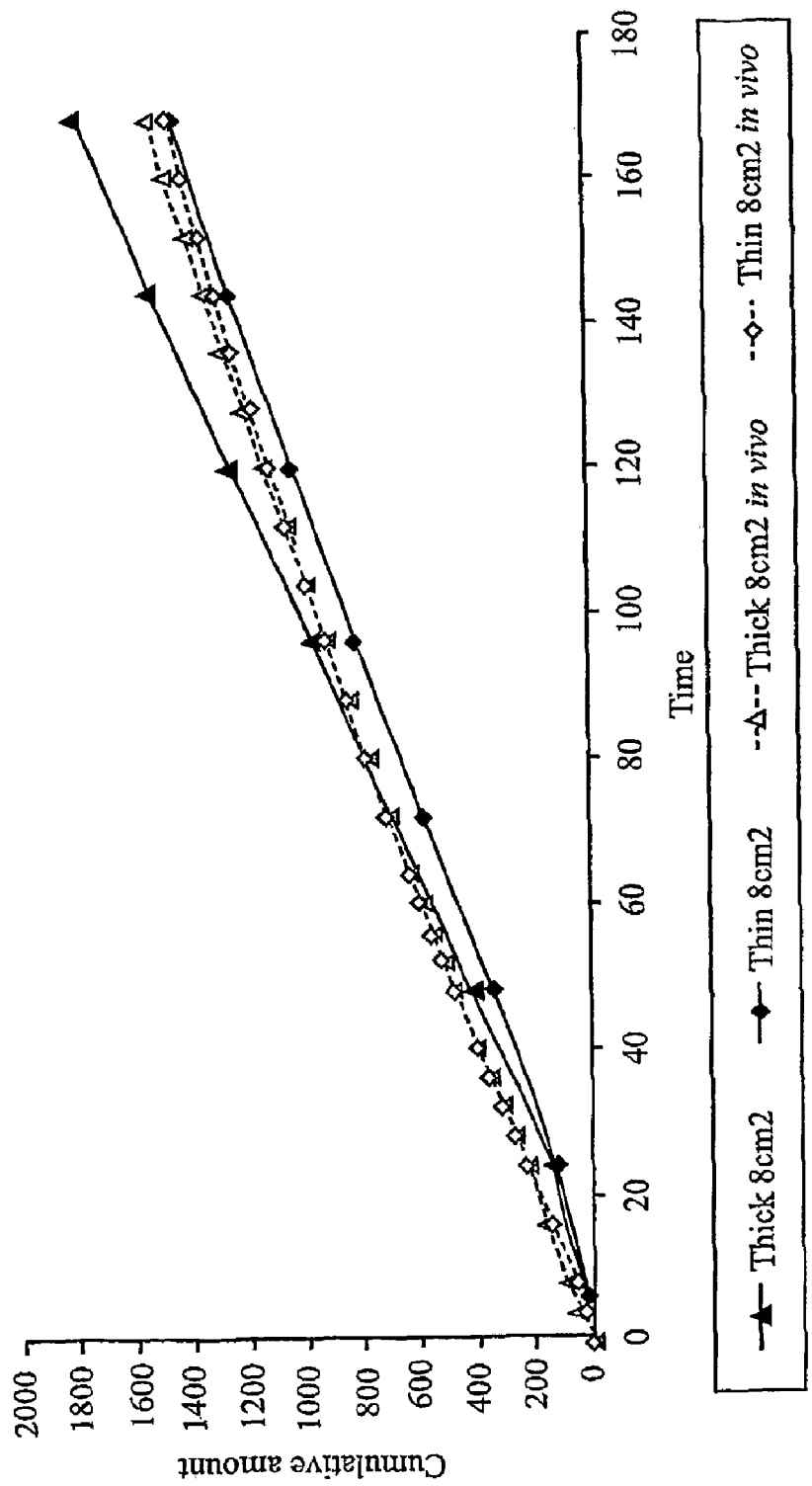
FIG. 10 depicts the in vitro cumulative release data (with breathable overlay) obtained in the Example 5 IVIVC study using the 2 and 8 cm$^2$ "thick" and "thin transdermal delivery systems.
Figure 11:
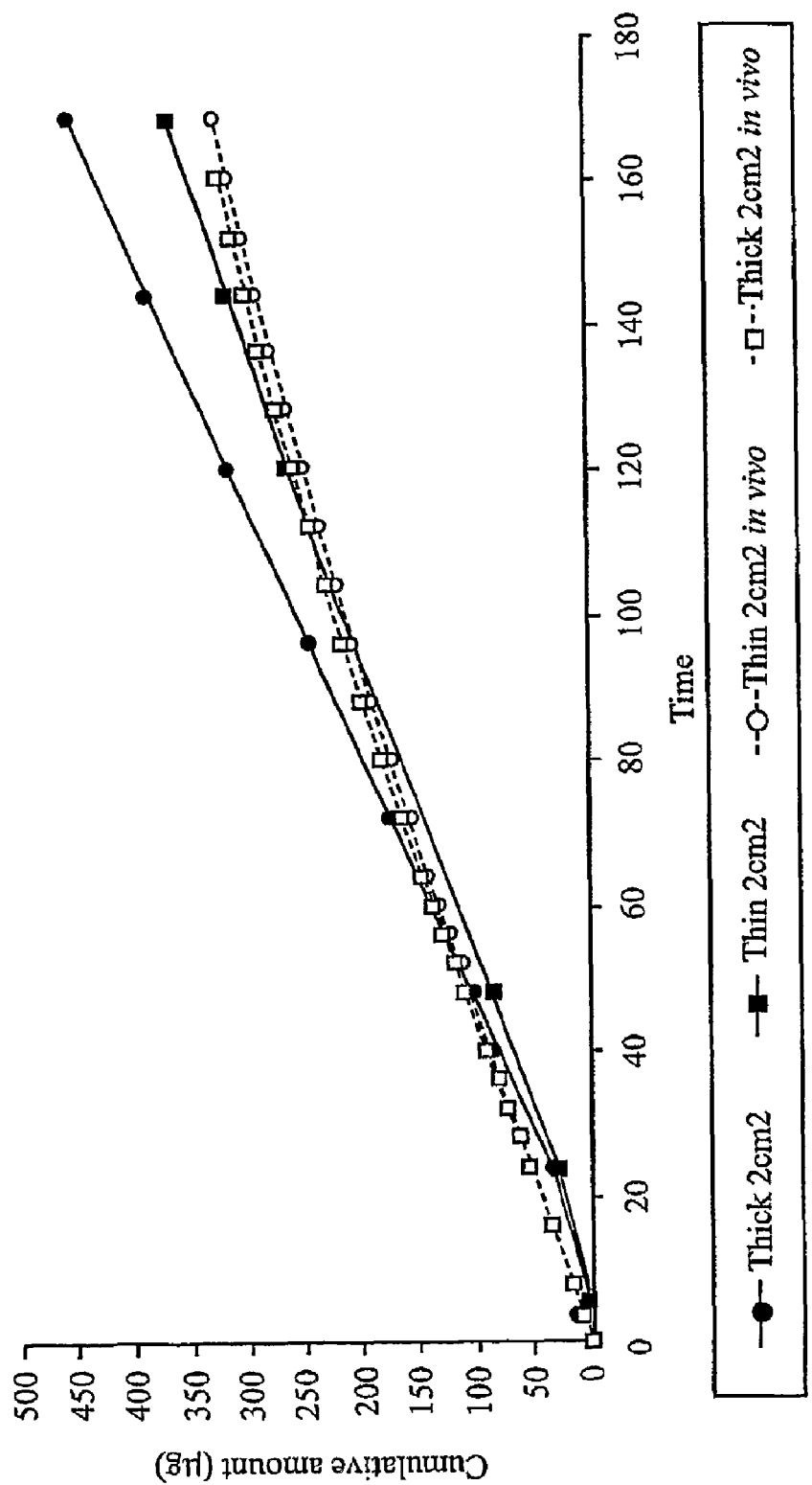
FIG. 11 depicts the in vivo input data obtained in the Example 5 IVIVC study using the 2 and 8 cm$^2$ "thick" and "thin transdermal delivery systems.
Figure 12:
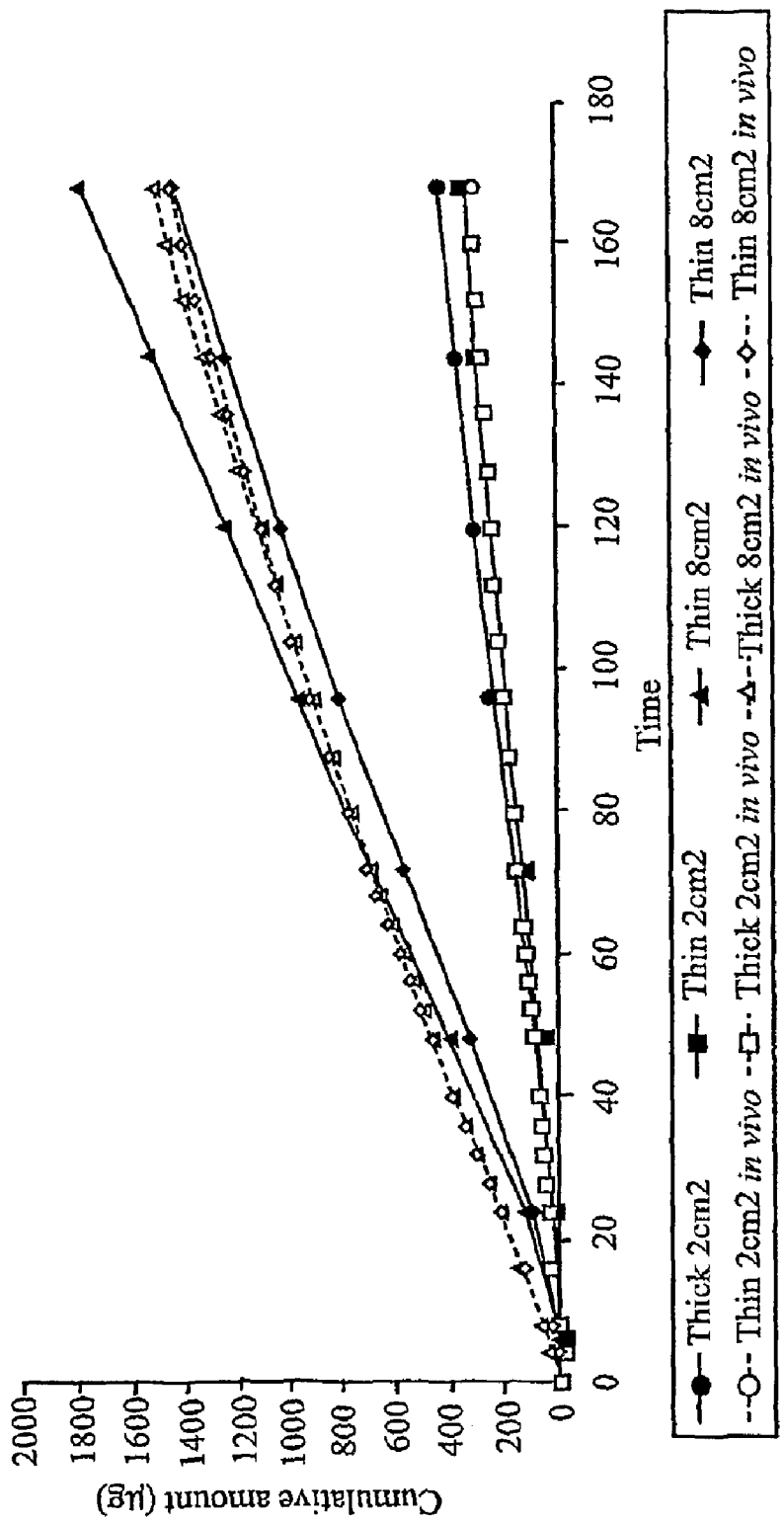
FIG. 12 depicts the in vitro and in vivo cumulative release data obtained in the Example 5 IVIVC study using the 2 and 8 cm$^2$ "thick" and "thin transdermal delivery systems.
Figure 13:
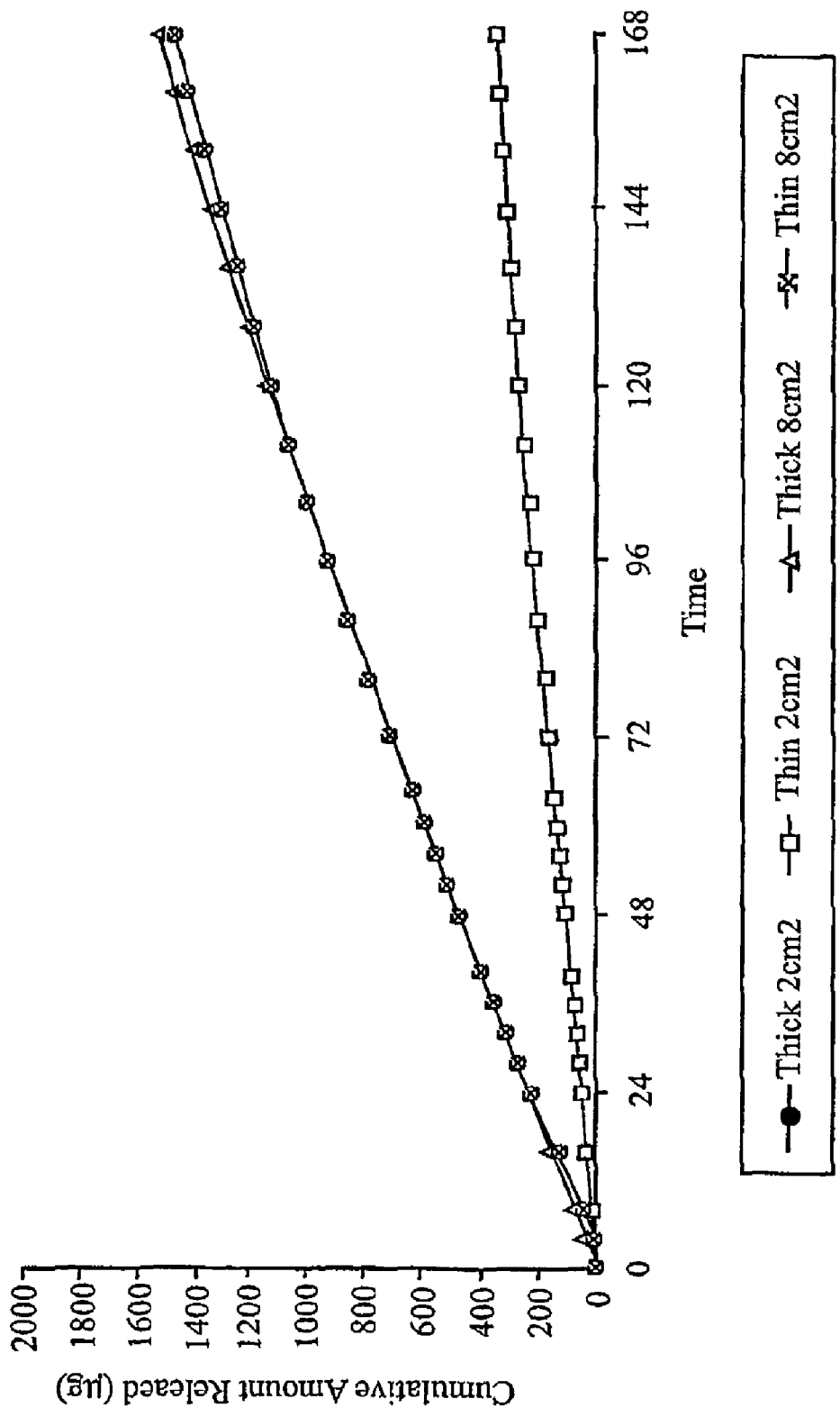
FIG. 13 depicts the in vitro and in vivo cumulative release data obtained in the Example 5 IVIVC study using the 2 cm$^2$ "thick" and "thin transdermal delivery systems.
Figure 14:
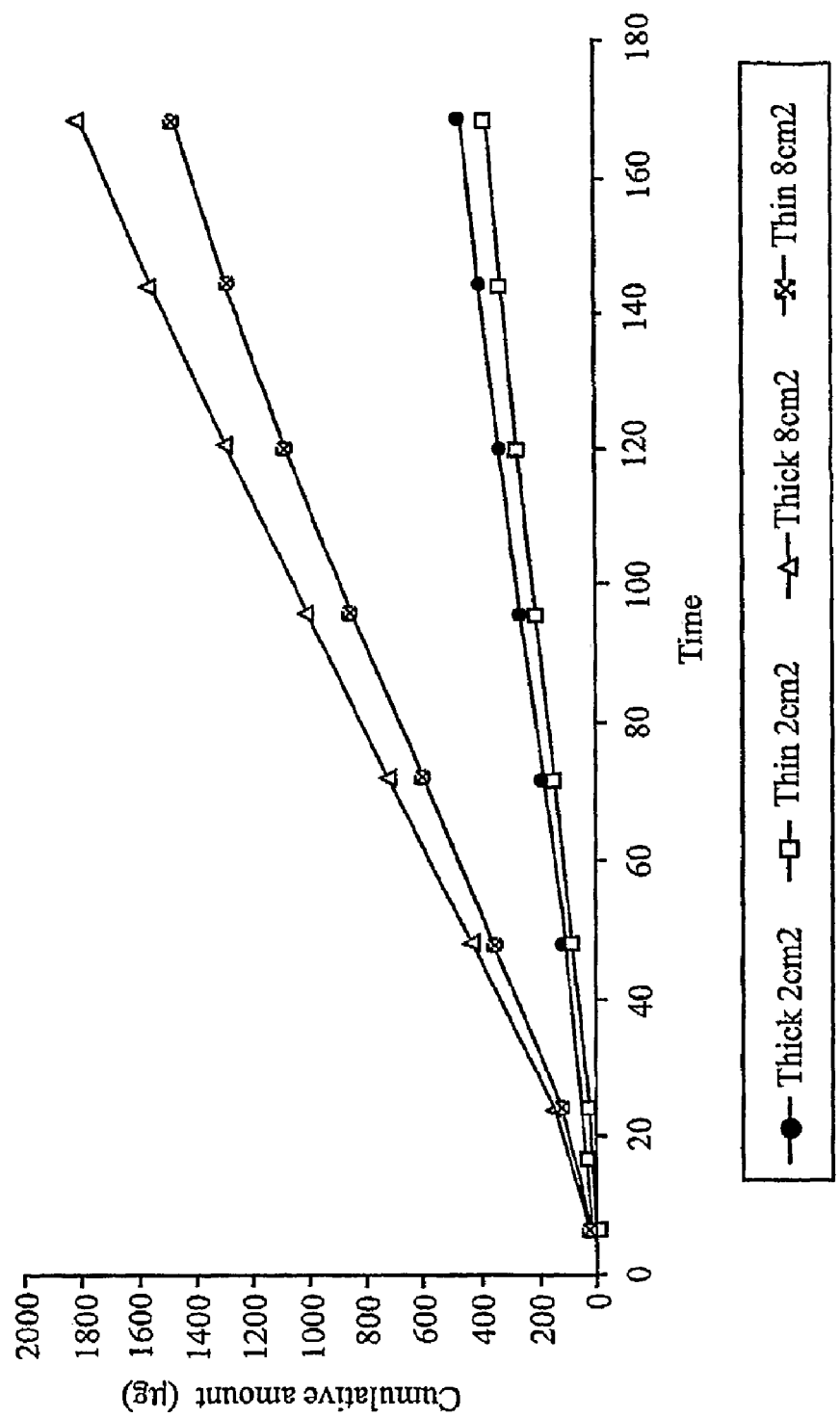
FIG. 14 depicts the in vitro and in vivo cumulative release data obtained in the Example 5 IVIVC study using the 8 cm$^2$ "thick" and "thin transdermal delivery systems.

The study was performed in 24 healthy human volunteers, broken up into four test groups of 6 individuals each (n=6), wherein the sufentanil patches were applied to the chest of the subjects that had been blocked with naloxone. In order to ensure that the patches remained in place, breathable overlay tape was used for each subject. The study was initiated with a low dose intravenous (IV) infusion of sufentanil (48 µg/6 hours) followed by application of the 2 cm² thick and thin patches, or a high dose IV infusion of sufentanil (192 µg/6 hours) followed by application of the 8 cm² thick and thin patches. The patches were left in place for 7 days and individual plasma sufentanil levels for each test subject were assessed-periodically over the 7-day study period using standard LC/MS methodologies. The individual sufentanil plasma levels observed for the subjects that wore the 2 cm² patches are reported in Table 7 below, and the individual sufentanil plasma levels observed for the subjects that wore the 8 cm² patches are reported in Table 8 below. The average and standard deviation sufentanil plasma levels for all four of the test groups are reported in Table 9 below, and the average plasma levels across days 1-7 of the study are reported in Table 10 below. FIG. 7 depicts the measured sufentanil plasma levels for the subjects that wore the thin patches, and FIG. 8 depicts the measured sufentanil plasma levels for the subjects that wore the thick patches. Finally, FIG. 9 depicts the average sufentanil plasma levels from all four test groups.

TABLE 7

Sufentanil Plasma Levels in Normal Volunteers after Application of Sufentanil TTS for 7 Days

| | | Lot 24A, 2 cm² - Thin Patches | | | | | | Lot 25A, 2 cm² - Thick Patches | | | | | |
|---|---|---|---|---|---|---|---|---|---|---|---|---|---|
| Time (Hours) | Time (Days) | Subject 1 | Subject 2 | Subject 3 | Subject 4 | Subject 5 | Subject 6 | Subject 7 | Subject 8 | Subject 9 | Subject 10 | Subject 11 | Subject 12 |
| 0 | 0.00 | 0 | 0 | 0 | 2.83 | 3.05 | 2.10 | 0 | 0 | 0 | 0 | 2.03 | 0 |
| 4 | 0.17 | 4.27 | 5.06 | 0 | 2.66 | 8.12 | 4.28 | 5.71 | 2.15 | 2.82 | 3.07 | 5.52 | 4.30 |
| 8 | 0.33 | 13.6 | 13.2 | 5.61 | 4.91 | 26.2 | 5.72 | 14.2 | 11.6 | 15.8 | 8.83 | 15.6 | 14.9 |
| 16 | 0.67 | 18.3 | 26.7 | 11.4 | 16.7 | 30.6 | 11.3 | 18.4 | 23.5 | 18.6 | 15.9 | 15.6 | 20.0 |
| 24 | 1.00 | 26.4 | 33.6 | 20.7 | 23.5 | 54.3 | 14.4 | 22.8 | 30.0 | 28.5 | 16.9 | 27.0 | 22.7 |
| 28 | 1.17 | 22.8 | 32.5 | 22.9 | 24.4 | 34.0 | 20.0 | 22.6 | 32.0 | 27.8 | 17.6 | 27.1 | 26.0 |
| 32 | 1.33 | 20.5 | 26.2 | 20.4 | 32.5 | 33.1 | 13.9 | 19.8 | 31.6 | 31.8 | 19.7 | 27.4 | 23.9 |
| 36 | 1.50 | 22.3 | 25.3 | 29.3 | 31.9 | 35.2 | 20.9 | 20.8 | 32.6 | 27.9 | 20.3 | 28.9 | 27.0 |
| 40 | 1.67 | 17.6 | 23.1 | 19.0 | 36.5 | 33.5 | 19.6 | 21.8 | 28.8 | 29.4 | 16.7 | 24.0 | 35.1 |
| 48 | 2.00 | 23.3 | 32.2 | 25.9 | 40.7 | 48.4 | 19.0 | 22.1 | 34.2 | 33.2 | 16.1 | 33.9 | 23.4 |
| 52 | 2.17 | 18.9 | 32.5 | 25.9 | 42.4 | 47.9 | 24.0 | 32.2 | 35.7 | 37.9 | 20.2 | 30.3 | 25.5 |
| 56 | 2.33 | 22.9 | 43.1 | 31.5 | 33.7 | 45.3 | 21.7 | 26.5 | 37.3 | 34.1 | 20.6 | 30.6 | 19.6 |
| 60 | 2.50 | 17.8 | 36.5 | 22.8 | 35.8 | 39.9 | 14.2 | 21.6 | 32.5 | 31.8 | 20.5 | 30.0 | 23.4 |
| 64 | 2.67 | 22.8 | 36.1 | 25.3 | 43.2 | 34.1 | 18.9 | 21.8 | 33.2 | 26.5 | 20.0 | 29.4 | 18.5 |
| 72 | 3.00 | 21.8 | 29.3 | 25.8 | 56.0 | 43.3 | 25.4 | 19.3 | 39.3 | 36.2 | 17.1 | 30.3 | 33.0 |
| 80 | 3.33 | 13.7 | 30.3 | 31.1 | 43.3 | 35.3 | 19.2 | 21.3 | 36.5 | 27.4 | 16.0 | 30.0 | 28.6 |
| 88 | 3.67 | 18.8 | 29.2 | 21.8 | 50.2 | 33.6 | 17.2 | 27.9 | 35.5 | 33.7 | 20.2 | 28.3 | 28.0 |
| 96 | 4.00 | 13.3 | 31.1 | 37.0 | 54.2 | 39.0 | 32.8 | 16.9 | 37.0 | 33.4 | 21.0 | 33.1 | 30.8 |
| 104 | 4.33 | 14.6 | 28.9 | 39.1 | 54.5 | 35.6 | 25.6 | 14.0 | 34.8 | 26.7 | 18.8 | 28.3 | 22.5 |
| 112 | 4.67 | 12.0 | 26.3 | 26.8 | 39.4 | 31.4 | 26.2 | 23.4 | 27.4 | 31.2 | 19.8 | 26.9 | 20.7 |
| 120 | 5.00 | 18.7 | 31.3 | 27.6 | 56.1 | 40.8 | 21.2 | 24.9 | 32.8 | 23.5 | 21.5 | 32.6 | 23.5 |
| 128 | 5.33 | 11.4 | 36.9 | 28.3 | 44.2 | 35.4 | 16.3 | 21.8 | 33.2 | 23.6 | 19.9 | 30.5 | 18.9 |
| 136 | 5.67 | 13.9 | 24.1 | 28.3 | 33.2 | 31.7 | 15.4 | 23.4 | 28.4 | 29.1 | 19.9 | 25.7 | 15.8 |
| 144 | 6.00 | 15.5 | 29.0 | 27.1 | 41.8 | 39.2 | 26.8 | 15.1 | 31.9 | 33.2 | 17.8 | 28.3 | 24.2 |
| 152 | 6.33 | 18.0 | 29.0 | 27.5 | 41.7 | 35.5 | 22.3 | 16.5 | 26.4 | 16.9 | 19.5 | 23.4 | 24.1 |
| 160 | 6.67 | 12.6 | 26.3 | 23.3 | 36.9 | 36.6 | 22.1 | 21.2 | 30.6 | 19.9 | 22.7 | 23.7 | 24.7 |

TABLE 8

Sufentanil Plasma Levels in Normal Volunteers after Application of Sufentanil TTS for 7 Days

| | | Lot 24B, 8 cm² - Thin Patches | | | | | | Lot 25B, 8 cm² - Thick Patches | | | | | |
|---|---|---|---|---|---|---|---|---|---|---|---|---|---|
| Time Hours | Time Days | Subject 13 | Subject 14 | Subject 15 | Subject 16 | Subject 17 | Subject 18 | Subject 19 | Subject 20 | Subject 21 | Subject 22 | Subject 23 | Subject 24 |
| 0 | 0.00 | 4.93 | 3.87 | 6.26 | 2.78 | 8.02 | 4.76 | 4.20 | 7.02 | 5.66 | 9.61 | 5.69 | 9.06 |
| 4 | 0.17 | 12.6 | 10.9 | 6.82 | 14.8 | 21.9 | 18.8 | 15.7 | 34.3 | 10.1 | | 18.9 | 39.9 |
| 8 | 0.33 | 57.2 | 38.3 | 12.1 | 40.9 | 60.1 | 60.7 | 47.8 | 67.2 | 47.1 | 36.1 | 205 | 142 |
| 16 | 0.67 | 83.1 | 86.3 | 58.0 | 83.9 | 68.0 | 88.2 | 78.3 | 94.2 | 102 | 73.7 | 93.7 | 126 |
| 24 | 1.00 | 79.1 | 145 | 91.9 | 74.8 | 78.5 | 150 | 106 | 81.0 | 124 | 135 | 108 | 163 |
| 28 | 1.17 | 112 | 110 | 90.0 | 98.4 | 112 | 110 | 116 | 91.7 | 127 | 108 | 132 | 152 |
| 32 | 1.33 | 101 | 113 | 97.7 | 113 | 85.2 | 121 | 114 | 99.5 | 126 | 138 | 152 | 190 |
| 36 | 1.50 | 103 | 118 | 94.6 | 99.0 | 93.8 | 137 | 109 | 104 | 137 | 150 | 125 | 152 |
| 40 | 1.67 | 89.0 | 108 | 110 | 128 | 95.4 | 120 | 101 | 89.3 | 150 | 128 | 122 | 170 |
| 48 | 2.00 | 99.7 | 131 | 96.4 | 96.1 | 89.3 | 127 | 110 | 92.7 | 157 | 124 | 145 | 189 |

TABLE 8-continued

Sufentanil Plasma Levels in Normal Volunteers after Application of Sufentanil TTS for 7 Days

| | | Lot 24B, 8 cm² - Thin Patches | | | | | | Lot 25B, 8 cm² - Thick Patches | | | | | |
|---|---|---|---|---|---|---|---|---|---|---|---|---|---|
| Time Hours | Time Days | Subject 13 | Subject 14 | Subject 15 | Subject 16 | Subject 17 | Subject 18 | Subject 19 | Subject 20 | Subject 21 | Subject 22 | Subject 23 | Subject 24 |
| 52 | 2.17 | 97.3 | 112 | 120 | 107 | 82.8 | 123 | 110 | 111 | 178 | 136 | 106 | 158 |
| 56 | 2.33 | 112 | 94.7 | 115 | 149 | 87.4 | 135 | 94.7 | 108 | 156 | 129 | 159 | 180 |
| 60 | 2.50 | 113 | 91.8 | 108 | 95.2 | 93.6 | 130 | 88.3 | 88.9 | 120 | 118 | 112 | 149 |
| 64 | 2.67 | 117 | 94.3 | 122 | 138 | 99.3 | 128 | 109 | 74.6 | 138 | 107 | 157 | 135 |
| 72 | 3.00 | 116 | 113 | 116 | 118 | 89.7 | 103 | 91.9 | 105 | 140 | 199 | 116 | 180 |
| 80 | 3.33 | 99.3 | 96.4 | 124 | 147 | 95.2 | 120 | 89.9 | 93.3 | 132 | 200 | 131 | 155 |
| 88 | 3.67 | 98.9 | 104 | 105 | 117 | 94.8 | 86.0 | 83.6 | 80.1 | 113 | 155 | 133 | 135 |
| 96 | 4.00 | 119 | 130 | 107 | 127 | 88.2 | 93.5 | 103 | 83.6 | 141 | 197 | 150 | 134 |
| 104 | 4.33 | 105 | 103 | 124 | 133 | 93.1 | 79.0 | 87.6 | 80.3 | 135 | 186 | 174 | 150 |
| 112 | 4.67 | 94.4 | 95.6 | 114 | 143 | 80.9 | 65.4 | 97.1 | 73.1 | 129 | 243 | 149 | 150 |
| 120 | 5.00 | 113 | 88.5 | 150 | 108 | 86.2 | 92.2 | 105 | 88.8 | 160 | 326 | 155 | 140 |
| 128 | 5.33 | 106 | 103 | 150 | 139 | 88.1 | 96.4 | 81.6 | 67.6 | 114 | 300 | 160 | 148 |
| 136 | 5.67 | 90.1 | 79.0 | 127 | 112 | 69.1 | 77.4 | 83.2 | 59.4 | 93.0 | 280 | 120 | 107 |
| 144 | 6.00 | 82.8 | 93.1 | 167 | 146 | 66.0 | 96.0 | 98.8 | 70.9 | 128 | 310 | 148 | 111 |
| 152 | 6.33 | 85.4 | 86.8 | 117 | 135 | 89.4 | 61.4 | 69.2 | 75.5 | 108 | 342 | 128 | 104 |
| 160 | 6.67 | 79.8 | 85.9 | 102 | 153 | 76.3 | 70.1 | 76.2 | 63.0 | 125 | 246 | 136 | 106 |

TABLE 9

Average Plasma Levels for Sufentanil TTS

| Time | Time | Lot 24A, 2 cm² Thin Patches | | Lot 25A, 2 cm² Thick Patches | | Lot 24B, 8 cm² Thin Patches | | Lot 25B, 8 cm² Thick Patches | |
|---|---|---|---|---|---|---|---|---|---|
| (Hours) | (Days) | Average | SD | Average | SD | Average | SD | Average | SD |
| 0 | 0.00 | 1.3 | 1.5 | 0.3 | 0.8 | 5.1 | 1.8 | 6.9 | 2.1 |
| 4 | 0.17 | 4.1 | 2.7 | 3.9 | 1.5 | 14.3 | 5.5 | 23.8 | 12.7 |
| 8 | 0.33 | 11.5 | 8.2 | 13.5 | 2.7 | 44.9 | 18.8 | 90.9 | 67.8 |
| 16 | 0.67 | 19.2 | 8.0 | 18.7 | 2.9 | 77.9 | 12.1 | 94.7 | 18.7 |
| 24 | 1.00 | 28.8 | 14.0 | 24.7 | 4.8 | 103.2 | 34.8 | 119.5 | 28.1 |
| 28 | 1.17 | 26.1 | 5.7 | 25.5 | 4.9 | 105.4 | 9.1 | 121.1 | 20.8 |
| 32 | 1.33 | 24.4 | 7.6 | 25.7 | 5.5 | 105.2 | 13.0 | 136.6 | 31.9 |
| 36 | 1.50 | 27.5 | 5.6 | 26.3 | 4.8 | 107.6 | 16.9 | 129.5 | 20.4 |
| 40 | 1.67 | 24.9 | 8.1 | 26.0 | 6.5 | 108.4 | 14.6 | 126.7 | 30.0 |
| 48 | 2.00 | 31.6 | 11.2 | 27.2 | 7.7 | 106.6 | 17.7 | 136.3 | 34.7 |
| 52 | 2.17 | 31.9 | 11.3 | 30.3 | 6.6 | 107.0 | 15.0 | 133.2 | 29.7 |
| 56 | 2.33 | 33.0 | 9.9 | 28.1 | 7.2 | 115.5 | 23.4 | 137.8 | 32.8 |
| 60 | 2.50 | 27.8 | 10.9 | 26.6 | 5.4 | 105.3 | 14.8 | 112.7 | 22.6 |
| 64 | 2.67 | 30.1 | 9.2 | 24.9 | 5.8 | 116.4 | 16.8 | 120.1 | 29.2 |
| 72 | 3.00 | 33.6 | 13.3 | 29.2 | 9.1 | 109.3 | 11.0 | 138.7 | 42.9 |
| 80 | 3.33 | 28.8 | 10.8 | 26.6 | 7.1 | 113.7 | 20.5 | 133.5 | 41.0 |
| 88 | 3.67 | 28.5 | 12.4 | 28.9 | 5.4 | 101.0 | 10.5 | 116.6 | 30.1 |
| 96 | 4.00 | 34.6 | 13.3 | 28.7 | 7.9 | 110.8 | 17.5 | 134.8 | 39.4 |
| 104 | 4.33 | 33.1 | 13.5 | 24.2 | 7.4 | 106.2 | 19.8 | 135.5 | 43.8 |
| 112 | 4.67 | 27.0 | 8.9 | 24.9 | 4.4 | 98.9 | 27.0 | 140.2 | 58.7 |
| 120 | 5.00 | 32.6 | 13.9 | 26.5 | 4.9 | 106.3 | 24.0 | 162.5 | 84.9 |
| 128 | 5.33 | 28.8 | 12.7 | 24.7 | 5.9 | 113.8 | 24.8 | 145.2 | 83.9 |
| 136 | 5.67 | 24.4 | 8.2 | 23.7 | 5.1 | 92.4 | 22.5 | 123.8 | 79.3 |
| 144 | 6.00 | 29.9 | 9.5 | 25.1 | 7.4 | 108.5 | 39.2 | 144.5 | 85.2 |
| 152 | 6.33 | 29.0 | 8.6 | 21.1 | 4.1 | 95.8 | 26.1 | 137.8 | 102.4 |
| 160 | 6.67 | 26.3 | 9.3 | 23.8 | 3.7 | 94.5 | 30.6 | 125.4 | 65.3 |

TABLE 10

Average Plasma Values for Sufentanil TTS from Days 1 to 7

| Lot Number | Lot Description | Average (pg/mL) | SD |
|---|---|---|---|
| 24A | 2 cm², thin | 29.2 | 10.1 |
| 25A | 2 cm², thick | 25.9 | 5.9 |
| 24B | 8 cm², thin | 105.0 | 21.1 |
| 25B | 8 cm², thick | 133.3 | 51.7 |

As can be seen by a review of the data presented in Tables 7-10, there is no significant difference in the sufentanil plasma levels achieved between the 2 cm² transdermal patches, even though the thick patches (Lot 25A) had about 75% greater sufentanil drug content as compared with the thin patches (Lot 24A). This same observation can be made with regard to the 8 cm² transdermal patches. As can also be seen with regard to the data depicted in FIGS. 7-9, the in vivo flux of sufentanil from the patches (both thick and thin) remained essentially constant across a single application administration period of at least about 7 days. Furthermore, with regard to the data presented in Tables 7-10, it can be seen that the transdermal patches were able to provide a substantially constant delivery rate of sufentanil over a single application administration period of at least about 48 hours to up to 7 days, where that constant delivery rate was sufficient to establish and maintain a plasma sufentanil concentration having a maximum to minimum ratio of about 1.8 or less over the relevant administration period.

Example 5

In Vitro/In Vivo Correlation Study for 7-Day Sufentanil Transdermal Delivery Systems In order to assess whether in vitro flux data obtained using the methods described in Examples 1 and 2 are predictive of the in vivo performance of the sufentanil transdermal delivery systems of the present invention as determined in Example 4 (in vitro/in vivo correlation, or "IVIVC"), the following modeling study was carried out. Since for many of the in vivo test subjects, detectable sufentanil concentrations were present at the time of the transdermal patch application (data not shown), the IVIVC model needed to account for such starting conditions to determine the input from the transdermal delivery systems. A compartmental modeling approach was used. With regard to the data, there was a need in the modeling to make an assumption regarding the structure of the transdermal delivery system input function (unlike a conventional deconvolution). Based upon a preliminary deconvolution, a 4 knot spline function was selected that allowed for both an initial lag and change in delivery rate over the 7 day duration of the in vivo studies. Thus, for each intravenous infusion (IV)/transdermal delivery system combination, the IV and the transdermal delivery data were modeled simultaneously using a two-compartment PK model. The typical input function from the transdermal delivery system was obtained, and correlated with in vitro cumulative release data obtained using the methods of Examples 1 and 2 to assess the thin and thick 2 and 8 cm$^2$ patches used in the in vivo studies described in Example 4. In order to remain consistent, the same breathable overlay tape used in the Example 4 studies was applied over the transdermal delivery systems placed on the Franz cell apparatus. The results of the IVIVC modeling study are depicted in FIGS. 10-14. As can be seen by a review of FIGS. 10-14, the in vitro cadaver skin flux data obtained using the methods of Examples 1 and 2 is representative of the in vivo input from the transdermal delivery systems of the present invention. In this regard, the average skin flux of sufentanil observed in vivo for the 2 and 8 cm$^2$ patches is approximately 1.1 μg/cm$^2$/hour.

What is claimed is:

1. A transdermal delivery system, comprising:
    a pressure sensitive adhesive matrix comprising sufentanil in an amount above the saturation point of sufentanil in the matrix, wherein the matrix consists of
       both dissolved and undissolved sufentanil,
       a blend of high molecular weight polyisobutylene and low molecular weight polyisobutylene, the high molecular weight polyisobutylene having a viscosity average molecular weight of about 450,000 to 2,100,000, the low molecular weight polyisobutylene having a viscosity average molecular weight of about 1,000 to 450,000,
       polybutene, and
       silicon dioxide;
    wherein the system provides a substantially zero order delivery rate of sufentanil over a single application administration period of at least about 48 hours; and
    wherein the system does not comprise a rate controlling membrane.

2. The transdermal delivery system of claim 1, wherein the system does not contain a permeation enhancer.

3. The transdermal delivery system of claim 1, wherein the sufentanil is present in the system in an amount of about 1 to about 20 weight percent relative to the total system.

4. The transdermal delivery system of claim 1, wherein the high molecular weight polyisobutylene has a viscosity average molecular weight of about 1,100,000.

5. The transdermal delivery system of claim 1, wherein the low molecular weight polyisobutylene has a viscosity average molecular weight of about 50,000 to 55,000.

6. The transdermal delivery system of claim 1, wherein the adhesive matrix has a drug releasing interface surface area of 40 cm$^2$ or less.

7. The transdermal delivery system of claim 1, wherein the system comprises a reservoir having a volume of about 0.0025 to 0.154 ml.

8. The transdermal delivery system of claim 1, wherein the delivery rate at steady state is at least about 1 μg/hour.

9. The transdermal delivery system of claim 8, wherein the delivery rate at steady state is at least about 1.5 μg/hour.

10. The transdermal delivery system of claim 9, wherein the delivery rate at steady state is at least about 2 μg/hour.

11. The transdermal delivery system of claim 1, wherein net flux from the system through the skin is at least about 1 μg/cm$^2$/hour.

12. The transdermal delivery system of claim 1, wherein the matrix has a solubility for sufentanil of about 1 wt % to about 2 wt %.

13. A transdermal delivery system, comprising:
    a pressure sensitive adhesive matrix comprising sufentanil in an amount above the saturation point of sufentanil in the matrix, wherein the matrix consists of
       both dissolved and undissolved sufentanil,
       a blend of high molecular weight polyisobutylene and low molecular weight polyisobutylene, the high molecular weight polyisobutylene having a viscosity average molecular weight of about 1,100,000, the low molecular weight polyisobutylene having a viscosity average molecular weight of about 50,000 to 55,000,
       polybutene, and
       silicon dioxide;
    wherein the system does not comprise a rate controlling membrane.

14. The transdermal delivery system of claim 13, wherein the system provides a substantially zero order delivery rate of sufentanil over a single application administration period of at least about 48 hours.

15. The transdermal delivery system of claim 13, wherein the system does not contain a permeation enhancer.

16. The transdermal delivery system of claim 13, wherein the sufentanil is present in the system in an amount of about 1 to about 20 weight percent relative to the total system.

17. The transdermal delivery system of claim 13, wherein the adhesive matrix has a drug releasing interface surface area of 40 cm$^2$ or less.

18. The transdermal delivery system of claim 13, wherein the system comprises a reservoir having a volume of about 0.0025 to 0.154 ml.

19. The transdermal delivery system of claim 13, wherein the system provides a delivery rate at steady state of at least about 1 μg/hour.

20. The transdermal delivery system of claim 13, wherein the system provides a delivery rate at steady state of at least about 1.5 μg/hour.

21. The transdermal delivery system of claim 13, wherein the system provides a delivery rate at steady state of at least about 2 μg/hour.

22. The transdermal delivery system of claim 13, wherein net flux from the system through the skin is at least about 1 μg/cm$^2$/hour.

* * * * *